(12) United States Patent
Hess et al.

(10) Patent No.: US 10,912,543 B2
(45) Date of Patent: Feb. 9, 2021

(54) SURGICAL END EFFECTOR LOADING DEVICE AND TROCAR INTEGRATION

(71) Applicant: Ethicon Endo-Surgery, LLC, Guaynabo, PR (US)

(72) Inventors: Christopher J. Hess, Blue Ash, OH (US); Frederick E. Shelton, IV, Hillsboro, OH (US); Ryan A. Bledsoe, Cincinnati, OH (US); Jeffrey L. Savage, West Chester, OH (US); Craig T. Gates, West Chester, OH (US); Douglas E. Withers, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 249 days.

(21) Appl. No.: 14/930,963

(22) Filed: Nov. 3, 2015

(65) Prior Publication Data

US 2017/0119361 A1    May 4, 2017

(51) Int. Cl.
*A61B 17/00*   (2006.01)
*A61B 17/34*   (2006.01)
*A61B 90/00*   (2016.01)

(52) U.S. Cl.
CPC .............. *A61B 17/00* (2013.01); *A61B 17/34* (2013.01); *A61B 17/3423* (2013.01);
(Continued)

(58) Field of Classification Search
CPC . A61B 17/34; A61B 1/00087; A61B 1/00101; A61B 2017/00362; A61B 2017/2931; A61B 2017/3445–3449
See application file for complete search history.

(56) References Cited

U.S. PATENT DOCUMENTS 3,043,309 A   7/1962   McCarthy
3,358,676 A   12/1967  Frei et al.
(Continued)

FOREIGN PATENT DOCUMENTS

DE   101 49 421 A1   4/2003
EP   1 709 900 A1   10/2006
(Continued)

OTHER PUBLICATIONS

European Search Report for European Application No. 16196867.2, dated Apr. 3, 2017.
(Continued)

*Primary Examiner* — Katherine M Shi
*Assistant Examiner* — Lindsey Bachman
(74) *Attorney, Agent, or Firm* — Mintz Levin Cohn Ferris Glovsky adn Popeo, P.C.

(57) ABSTRACT

Devices and methods for delivering end effectors through surgical trocars are described herein. In one embodiment, a surgical end effector loading device is provided that includes a housing having a distal-facing first portion configured to couple with a proximal end of a surgical trocar, and an elongate second portion protruding distally from the first portion. The second portion can include a lumen formed therein and can be configured to extend into a working channel of the surgical trocar when the housing is coupled thereto. The device can also include at least one mating element coupled to the housing and configured to interface with a complementary mating element of the surgical trocar to restrict movement of the housing relative to the trocar, as well as an end effector retainer coupled to the housing and configured to selectively couple a surgical end effector to the housing.

7 Claims, 33 Drawing Sheets

(52) U.S. Cl.
CPC .... *A61B 90/08* (2016.02); *A61B 2017/00362* (2013.01); *A61B 2017/00486* (2013.01)

(56) References Cited

U.S. PATENT DOCUMENTS

| | | | |
|---|---|---|---|
| 3,710,399 A | 1/1973 | Hurst | |
| 3,893,448 A | 7/1975 | Brantigan | |
| 3,906,217 A | 9/1975 | Lackore | |
| 3,988,535 A | 10/1976 | Hickman et al. | |
| 4,047,136 A | 9/1977 | Satto | |
| 4,063,561 A | 12/1977 | McKenna | |
| 4,099,192 A | 7/1978 | Aizawa et al. | |
| 4,278,077 A | 7/1981 | Mizumoto | |
| 4,384,584 A | 5/1983 | Chen | |
| 4,585,282 A | 4/1986 | Bosley | |
| 4,597,390 A | 7/1986 | Mulhollan et al. | |
| 4,655,746 A | 4/1987 | Daniels et al. | |
| 5,052,402 A | 10/1991 | Bencini et al. | |
| 5,201,743 A | 4/1993 | Haber et al. | |
| 5,256,147 A * | 10/1993 | Vidal | A61B 17/3417 604/158 |
| 5,282,806 A | 2/1994 | Haber et al. | |
| 5,286,255 A | 2/1994 | Weber | |
| 5,308,357 A | 5/1994 | Lichtman | |
| 5,314,424 A | 5/1994 | Nicholas | |
| 5,330,502 A | 7/1994 | Hassler et al. | |
| 5,352,219 A | 10/1994 | Reddy | |
| 5,392,917 A | 2/1995 | Alpern et al. | |
| 5,417,203 A | 5/1995 | Tovey et al. | |
| 5,441,059 A | 8/1995 | Dannan | |
| 5,468,250 A | 11/1995 | Paraschac et al. | |
| 5,502,698 A | 3/1996 | Mochizuki | |
| 5,507,297 A | 4/1996 | Slater et al. | |
| 5,540,648 A | 7/1996 | Yoon | |
| 5,562,655 A | 10/1996 | Mittelstadt et al. | |
| 5,578,052 A | 11/1996 | Koros et al. | |
| 5,593,402 A | 1/1997 | Patrick | |
| 5,613,937 A | 3/1997 | Garrison et al. | |
| 5,618,303 A | 4/1997 | Marlow et al. | |
| 5,716,326 A | 2/1998 | Dannan | |
| 5,762,255 A | 6/1998 | Chrisman et al. | |
| 5,792,165 A | 8/1998 | Klieman et al. | |
| 5,810,877 A | 9/1998 | Roth et al. | |
| 5,881,615 A | 3/1999 | Dahl et al. | |
| 5,928,263 A | 7/1999 | Hoogeboom | |
| 5,980,455 A | 11/1999 | Daniel et al. | |
| 6,024,748 A | 2/2000 | Manzo et al. | |
| 6,059,719 A | 5/2000 | Yamamoto et al. | |
| 6,099,537 A | 8/2000 | Sugai et al. | |
| 6,159,200 A | 12/2000 | Verdura et al. | |
| 6,309,397 B1 | 10/2001 | Julian et al. | |
| 6,315,789 B1 | 11/2001 | Cragg | |
| 6,332,384 B1 | 12/2001 | Cluthe | |
| 6,419,688 B1 | 7/2002 | Bacher et al. | |
| 6,471,172 B1 | 10/2002 | Lemke et al. | |
| 6,589,211 B1 | 7/2003 | MacLeod | |
| 6,595,984 B1 | 7/2003 | DeGuillebon | |
| 6,626,824 B2 | 9/2003 | Ruegg et al. | |
| 6,635,071 B2 | 10/2003 | Boche et al. | |
| 6,656,198 B2 * | 12/2003 | Tsonton | A61B 17/3417 604/170.01 |
| 6,723,043 B2 | 4/2004 | Kleeman et al. | |
| 6,770,081 B1 | 8/2004 | Cooper et al. | |
| 6,776,165 B2 | 8/2004 | Jin | |
| 6,827,712 B2 | 12/2004 | Tovey et al. | |
| 6,860,878 B2 | 3/2005 | Brock | |
| 6,869,395 B2 | 3/2005 | Page et al. | |
| 6,884,213 B2 | 4/2005 | Raz et al. | |
| 6,936,003 B2 | 8/2005 | Iddan | |
| 6,942,674 B2 | 9/2005 | Belef et al. | |
| 6,986,738 B2 | 1/2006 | Glukhovsky et al. | |
| 6,994,708 B2 | 2/2006 | Manzo | |
| 7,039,453 B2 | 5/2006 | Mullick et al. | |
| 7,042,184 B2 | 5/2006 | Oleynikov et al. | |
| 7,066,879 B2 | 6/2006 | Fowler et al. | |
| 7,083,579 B2 | 8/2006 | Yokoi et al. | |
| 7,122,028 B2 | 10/2006 | Looper et al. | |
| 7,125,403 B2 | 10/2006 | Julian et al. | |
| 7,169,104 B2 | 1/2007 | Ueda et al. | |
| 7,199,545 B2 | 4/2007 | Oleynikov et al. | |
| 7,211,094 B2 | 5/2007 | Gannoe et al. | |
| 7,241,290 B2 | 7/2007 | Doyle et al. | |
| 7,297,142 B2 | 11/2007 | Brock | |
| 7,331,967 B2 | 2/2008 | Lee et al. | |
| 7,429,259 B2 | 9/2008 | Cadeddu et al. | |
| 7,448,993 B2 | 11/2008 | Yokoi et al. | |
| 7,559,887 B2 | 7/2009 | Dannan | |
| 7,566,331 B2 | 7/2009 | Looper et al. | |
| 7,604,642 B2 | 10/2009 | Brock | |
| 7,651,471 B2 | 1/2010 | Yokoi et al. | |
| 7,665,391 B2 | 2/2010 | Beauchamp | |
| 7,666,181 B2 | 2/2010 | Abou El Kheir | |
| 7,678,043 B2 | 3/2010 | Gilad | |
| 7,691,103 B2 | 4/2010 | Fernandez et al. | |
| 7,691,126 B2 | 4/2010 | Bacher | |
| 7,699,835 B2 | 4/2010 | Lee et al. | |
| 7,722,599 B2 | 5/2010 | Julian et al. | |
| 7,862,553 B2 | 1/2011 | Ewaschuk | |
| 7,894,882 B2 | 2/2011 | Mullick et al. | |
| 7,901,398 B2 | 3/2011 | Stanczak et al. | |
| 8,021,358 B2 | 9/2011 | Doyle et al. | |
| 8,034,032 B2 | 10/2011 | Voegele et al. | |
| 8,038,612 B2 | 10/2011 | Paz | |
| 8,052,636 B2 | 11/2011 | Moll et al. | |
| 8,057,502 B2 | 11/2011 | Maliglowka et al. | |
| 8,088,062 B2 | 1/2012 | Zwolinski | |
| 8,128,643 B2 | 3/2012 | Aranyi et al. | |
| 8,182,414 B2 | 5/2012 | Handa et al. | |
| 8,187,166 B2 | 5/2012 | Kuth et al. | |
| 8,377,044 B2 | 2/2013 | Coe et al. | |
| 8,397,335 B2 | 3/2013 | Gordin et al. | |
| 8,398,544 B2 | 3/2013 | Altamirano | |
| 8,409,076 B2 | 4/2013 | Pang et al. | |
| 8,475,361 B2 | 7/2013 | Barlow et al. | |
| 8,518,024 B2 | 8/2013 | Williams et al. | |
| 8,623,011 B2 | 1/2014 | Spivey | |
| 8,636,648 B2 | 1/2014 | Gazdzinski | |
| 8,721,539 B2 | 5/2014 | Shohat et al. | |
| 8,764,735 B2 | 7/2014 | Coe et al. | |
| 8,845,661 B2 | 9/2014 | D'Arcangelo et al. | |
| 9,142,527 B2 | 9/2015 | Lee et al. | |
| 9,282,879 B2 | 3/2016 | Farin et al. | |
| 9,308,011 B2 | 4/2016 | Chao et al. | |
| 9,408,628 B2 | 8/2016 | Altamirano | |
| 9,451,937 B2 | 9/2016 | Parihar | |
| 2001/0051766 A1 | 12/2001 | Gazdzinski | |
| 2003/0060702 A1 | 3/2003 | Kuth et al. | |
| 2003/0114731 A1 | 6/2003 | Cadeddu et al. | |
| 2004/0093039 A1 | 5/2004 | Schumert | |
| 2004/0133235 A1 | 7/2004 | Bacher | |
| 2004/0152941 A1 | 8/2004 | Asmus et al. | |
| 2005/0033354 A1 | 2/2005 | Montalvo et al. | |
| 2005/0070943 A1 * | 3/2005 | Hueil | A61B 17/3462 606/167 |
| 2005/0085697 A1 | 4/2005 | Yokoi et al. | |
| 2005/0119640 A1 | 6/2005 | Sverduk et al. | |
| 2005/0131396 A1 | 6/2005 | Stanczak et al. | |
| 2005/0165449 A1 | 7/2005 | Cadeddu et al. | |
| 2005/0215983 A1 | 9/2005 | Brock | |
| 2005/0250984 A1 | 11/2005 | Lam et al. | |
| 2005/0272972 A1 | 12/2005 | Iddan | |
| 2005/0272974 A1 | 12/2005 | Iddan | |
| 2005/0273139 A1 | 12/2005 | Krauss et al. | |
| 2005/0288555 A1 | 12/2005 | Binmoeller | |
| 2006/0079933 A1 | 4/2006 | Hushka et al. | |
| 2006/0149135 A1 | 7/2006 | Paz | |
| 2006/0184161 A1 | 8/2006 | Maahs et al. | |
| 2006/0190035 A1 | 8/2006 | Hushka et al. | |
| 2006/0195015 A1 | 8/2006 | Mullick et al. | |
| 2006/0229592 A1 | 10/2006 | Yokoi et al. | |
| 2006/0258905 A1 | 11/2006 | Kaji et al. | |
| 2007/0010709 A1 | 1/2007 | Reinschke | |
| 2007/0049966 A1 | 3/2007 | Bonadio et al. | |
| 2007/0073247 A1 | 3/2007 | Ewaschuk | |

(56) References Cited

U.S. PATENT DOCUMENTS

| | | |
|---|---|---|
| 2007/0093792 A1 | 4/2007 | Julian et al. |
| 2007/0123748 A1 | 5/2007 | Meglan |
| 2007/0156015 A1 | 7/2007 | Gilad |
| 2007/0255100 A1 | 11/2007 | Barlow et al. |
| 2007/0255273 A1 | 11/2007 | Fernandez et al. |
| 2007/0270651 A1 | 11/2007 | Gilad et al. |
| 2007/0299387 A1 | 12/2007 | Williams et al. |
| 2008/0015413 A1 | 1/2008 | Barlow et al. |
| 2008/0015552 A1 | 1/2008 | Doyle et al. |
| 2008/0045003 A1 | 2/2008 | Lee et al. |
| 2008/0140090 A1 | 6/2008 | Aranyi et al. |
| 2008/0142005 A1 | 6/2008 | Schnell |
| 2008/0154299 A1 | 6/2008 | Livneh |
| 2008/0242939 A1 | 10/2008 | Johnston |
| 2008/0243106 A1 | 10/2008 | Coe et al. |
| 2008/0287926 A1 | 11/2008 | Abou El Kheir |
| 2008/0312499 A1 | 12/2008 | Handa et al. |
| 2009/0005636 A1 | 1/2009 | Pang et al. |
| 2009/0005638 A1 | 1/2009 | Zwolinski |
| 2009/0093833 A1* | 4/2009 | Smith ................ A61B 17/3417 606/185 |
| 2009/0209947 A1 | 8/2009 | Gordin et al. |
| 2010/0147921 A1 | 6/2010 | Olson |
| 2010/0249700 A1* | 9/2010 | Spivey ............. A61B 17/00234 604/96.01 |
| 2010/0331883 A1* | 12/2010 | Schmitz ............. A61B 17/1604 606/249 |
| 2011/0040322 A1 | 2/2011 | Major |
| 2011/0087265 A1 | 4/2011 | Nobis et al. |
| 2011/0087266 A1 | 4/2011 | Conlon et al. |
| 2011/0087267 A1 | 4/2011 | Spivey et al. |
| 2011/0115891 A1 | 5/2011 | Trusty |
| 2011/0118756 A1* | 5/2011 | Brock .................... A61B 34/71 606/130 |
| 2011/0208007 A1 | 8/2011 | Shohat et al. |
| 2011/0230869 A1 | 9/2011 | Altamirano |
| 2011/0288560 A1 | 11/2011 | Shohat et al. |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078290 A1 | 3/2012 | Nobis et al. |
| 2012/0078291 A1* | 3/2012 | Nobis .................... A61B 17/29 606/206 |
| 2012/0083826 A1 | 4/2012 | Chao et al. |
| 2012/0088965 A1 | 4/2012 | Stokes et al. |
| 2012/0089093 A1 | 4/2012 | Trusty |
| 2012/0089176 A1* | 4/2012 | Sigmon, Jr. et al. .. A61B 17/08 606/205 |
| 2012/0095298 A1 | 4/2012 | Stefanchik et al. |
| 2012/0259325 A1 | 10/2012 | Houser et al. |
| 2012/0316575 A1 | 12/2012 | Farin et al. |
| 2013/0138091 A1 | 5/2013 | Coe et al. |
| 2014/0005474 A1 | 1/2014 | Farin et al. |
| 2014/0066711 A1 | 3/2014 | Farin et al. |
| 2014/0088569 A1 | 3/2014 | Parihar et al. |
| 2014/0088637 A1 | 3/2014 | Parihar et al. |
| 2014/0088638 A1 | 3/2014 | Parihar |
| 2014/0194685 A1 | 7/2014 | Riek et al. |
| 2014/0243799 A1 | 8/2014 | Parihar |
| 2014/0243800 A1 | 8/2014 | Parihar |
| 2014/0275791 A1* | 9/2014 | Lambrecht ......... A61B 17/3462 600/201 |
| 2014/0277018 A1* | 9/2014 | Parihar ............... A61B 17/3478 606/167 |
| 2014/0378953 A1 | 12/2014 | Coe et al. |
| 2015/0088191 A1 | 3/2015 | Coe et al. |
| 2017/0119360 A1 | 5/2017 | Hess et al. |

FOREIGN PATENT DOCUMENTS

| | | |
|---|---|---|
| JP | 2005-261734 A | 9/2005 |
| JP | 2008-518716 A | 6/2008 |
| WO | 2008/015666 A2 | 2/2008 |
| WO | 2010/060436 A1 | 6/2010 |
| WO | 2010/081482 A1 | 7/2010 |
| WO | 2010/111319 A1 | 9/2010 |
| WO | 2010/114634 A1 | 10/2010 |
| WO | 2011/044353 A1 | 4/2011 |
| WO | 2011/081702 A1 | 7/2011 |
| WO | 2011/089565 A1 | 7/2011 |
| WO | 2012/035524 A2 | 3/2012 |
| WO | 2012/040183 A1 | 3/2012 |
| WO | 2012/112622 A2 | 8/2012 |
| WO | 2012/126967 A2 | 9/2012 |
| WO | 2013/007764 A2 | 1/2013 |
| WO | 2013/048963 A2 | 4/2013 |
| WO | 2014/052177 A1 | 4/2014 |
| WO | 2015025178 A1 | 2/2015 |

OTHER PUBLICATIONS

International Search Report dated Mar. 21, 2011; International Application No. PCT/US2010/051812 (7 pages).
International Preliminary Report dated Apr. 19, 2012; International Application No. PCT/US2010/051812; (10 pages).
International Search Report dated Mar. 2, 2012; International Application No. PCT/US2011/050198 (7 pages).
International Preliminary Report dated Mar. 14, 2013; International Application No. PCT/US2011/050198 (10 pages).
International Search Report dated Dec. 12, 2011; International Application No. PCT/US2011/052327 (5 pages).
International Preliminary Report dated Apr. 4, 2013; International Application No. PCT/US2011/052327 (9 pages).
International Search Report dated Apr. 3, 2013; International Application No. PCT/US2012/056900 (3 pages).
International Preliminary Report dated Apr. 10, 2014; International Application No. PCT/US2012/056900 (8 pages).
International Search Report dated Dec. 20, 2013; International Application No. PCT/US2013/060803 (3 pages).
International Preliminary Report dated Apr. 9, 2015; International Application No. PCT/US2013/060803 (9 pages).
International Search Report dated May 28, 2014; International Application No. PCT/US2014/015738 (4 pages).
International Preliminary Report on Patentability dated Sep. 11, 2015; International Application No. PCT/US2014/015738 (12 pages).
US Application as filed on Oct. 9, 2009 for U.S. Appl. No. 12/576,529 (18 pages).

* cited by examiner

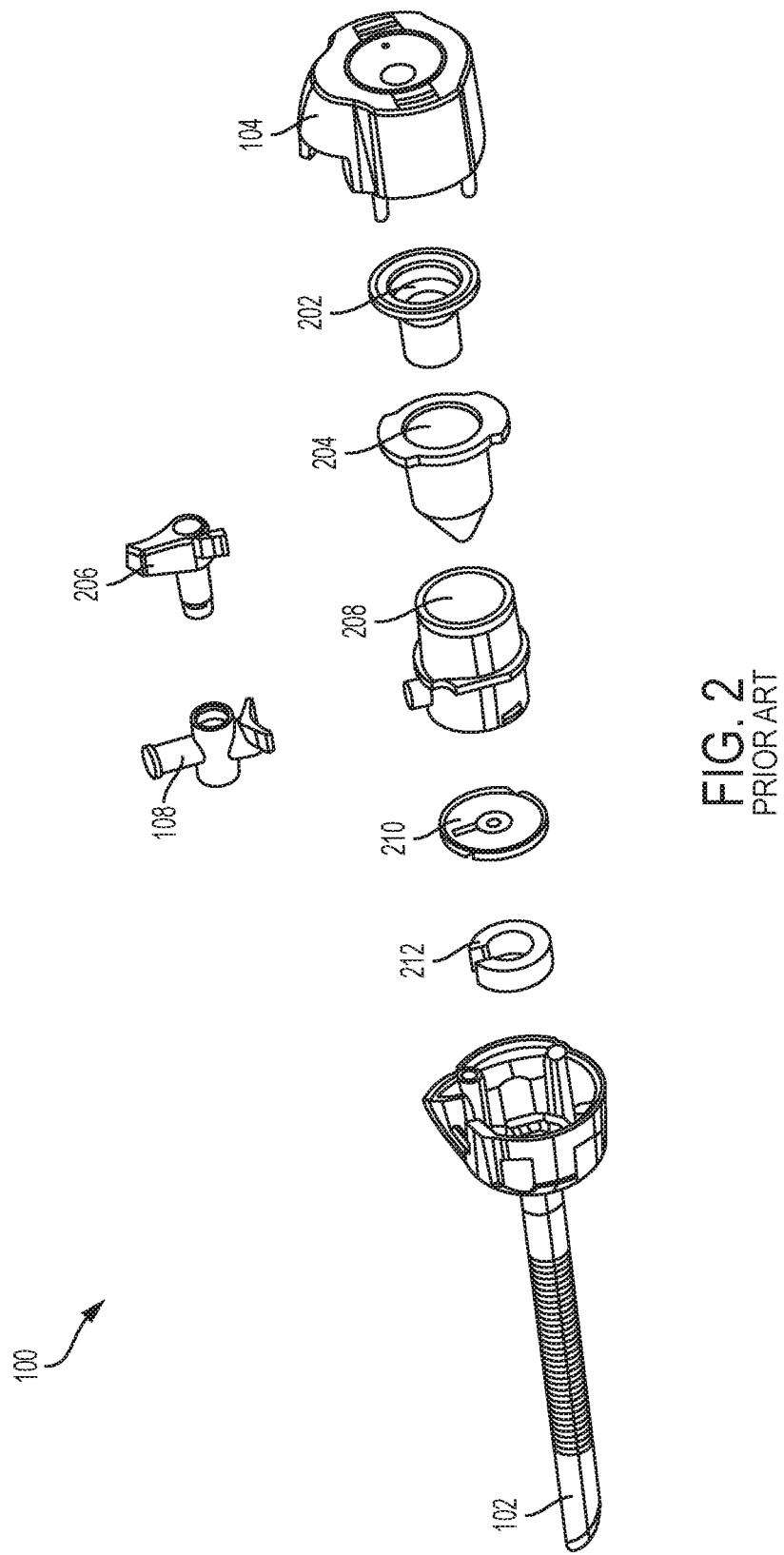

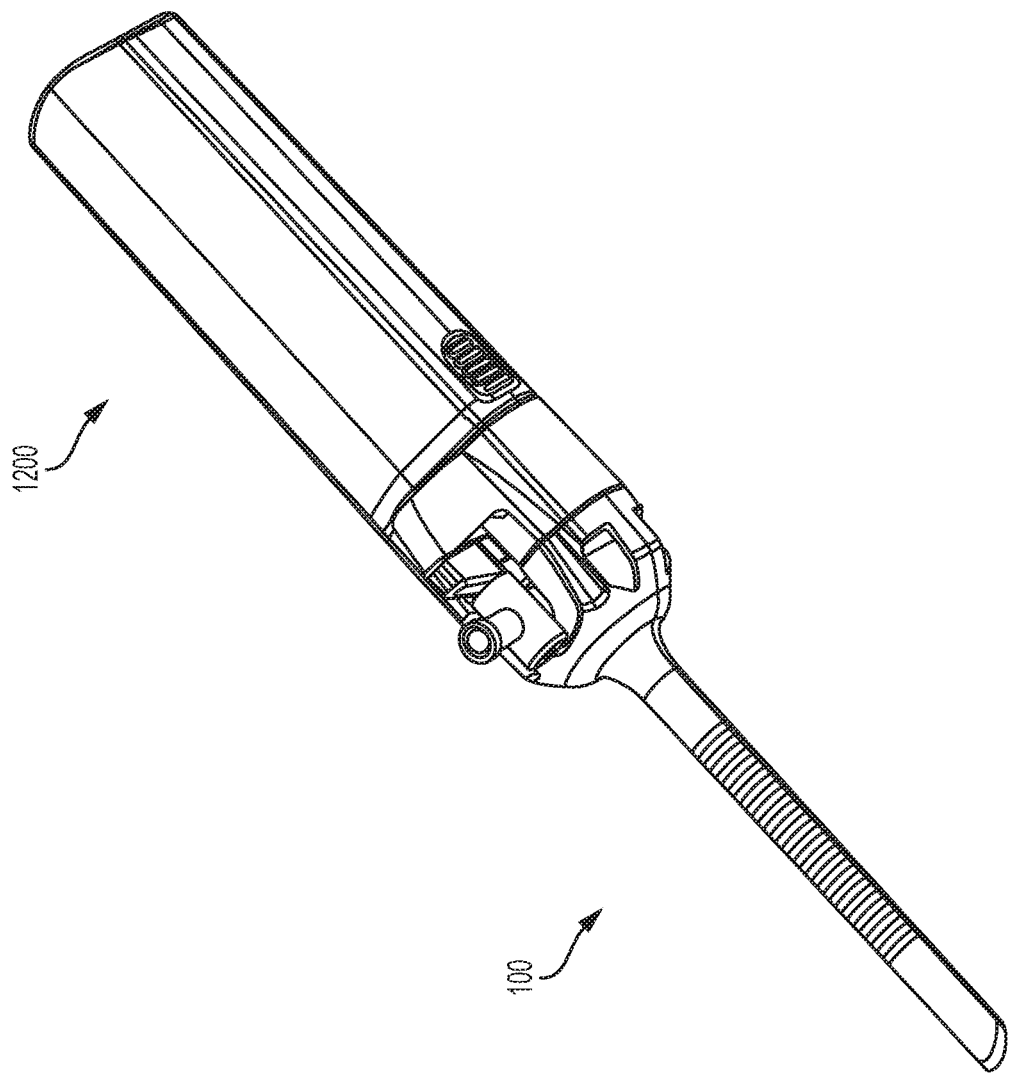

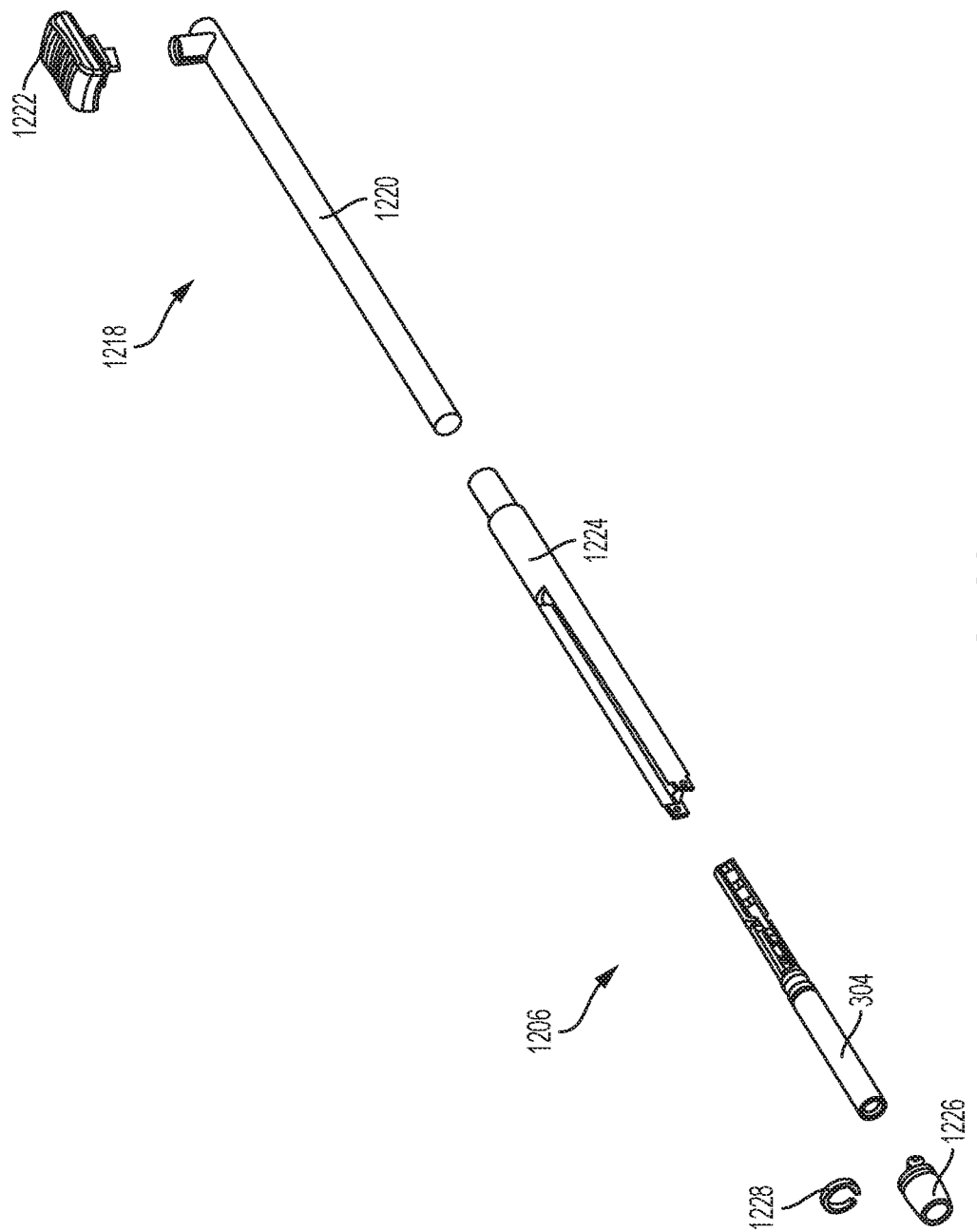

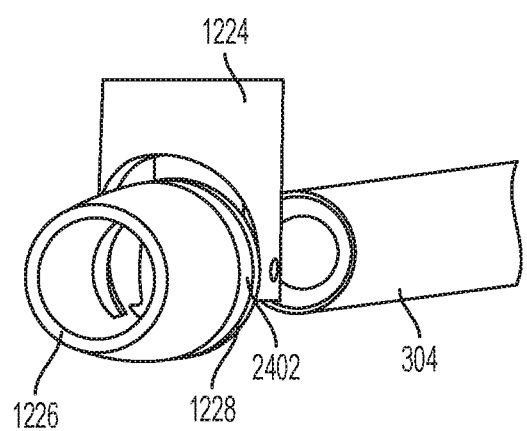
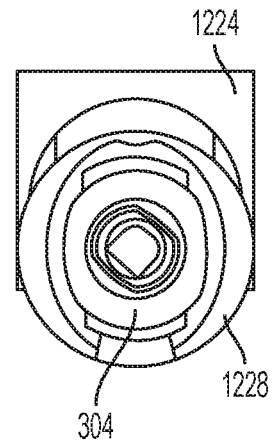
FIG. 25A  FIG. 25B
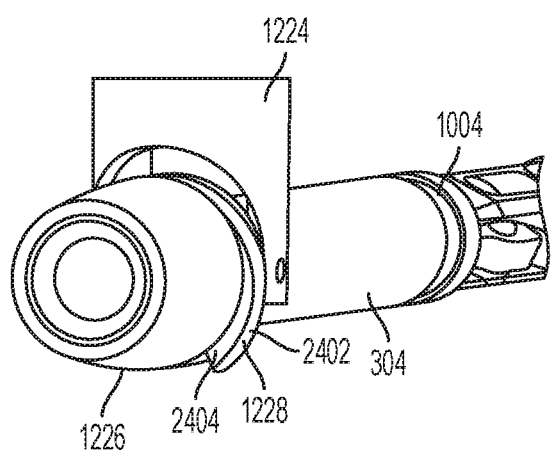
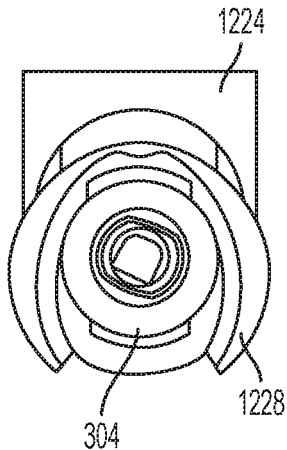
FIG. 26A  FIG. 26B

SURGICAL END EFFECTOR LOADING DEVICE AND TROCAR INTEGRATION

FIELD OF INVENTION

This disclosure relates generally to surgical instruments and, more particularly, to devices that deliver end effectors to a surgical site.

BACKGROUND

Surgical procedures are used to treat and cure a wide range of diseases, conditions, and injuries. Surgery often requires access to internal tissue through open or minimally invasive surgical procedures. The term "minimally invasive" refers to all types of minimally invasive surgical procedures, including endoscopic, laparoscopic, arthroscopic, natural orifice intraluminal, and natural orifice transluminal procedures. Minimally invasive surgery can have numerous advantages compared to traditional open surgical procedures, including reduced trauma, faster recovery, reduced risk of infection, and reduced scarring.

In many minimally invasive procedures, the abdominal cavity is insufflated with carbon dioxide gas to provide adequate space to perform a procedure. The insufflated cavity is generally under pressure and is sometimes referred to as being in a state of pneumoperitoneum. Surgical access devices are often used to facilitate surgical manipulation of internal tissue while maintaining pneumoperitoneum. For example, during a surgical procedure the abdominal wall can be pierced and a cannula or trocar (such as the trocar shown in FIGS. 1A-2) can be inserted into the abdominal cavity. The trocar can provide a port through which other surgical instruments can be passed into a patient's body to perform a variety of procedures.

Development in minimally invasive surgery has resulted in increasingly complex procedures that require multiple instruments and precise manipulations within the body. Because of the limited access space afforded by a trocar and the relatively larger wound size associated therewith, one solution has been the use of percutaneous surgical instruments inserted directly into a body cavity and used to supplement instruments introduced through one or more trocars. For example, procedures have been developed that involve additional percutaneous instruments to aid in retracting organs and structures. In some procedures, one or more percutaneous instruments having removable end effectors are utilized in combination with a trocar that can accommodate the passage of various end effectors for connection with the instrument in vivo. Inserting surgical instruments percutaneously, i.e., passing directly through tissue without an access device, can further reduce trauma and scarring to the patient by reducing the size of the wound created. Additional details on such instruments can be found, for example, in U.S. Patent Application Publication No. 2011/0087267 to Spivey et al., entitled "Method For Exchanging End Effectors In Vivo," which is hereby incorporated by reference.

The increasing use of percutaneously-inserted surgical instruments is not without challenges, however. For example, it can be difficult to successfully attach or remove an end effector from a percutaneously-inserted instrument inside a patient's body. There are a number of reasons for this, not the least of which is the confined and remote environment in which the instrument shaft and end effector are being manipulated. In addition, exchanging end effectors can require a large operating staff, as it can be necessary to simultaneously manipulate the percutaneously-inserted instrument, the trocar providing access to pass an end effector, and a loading device used to deliver an end effector through the trocar and attach it to a distal end of the instrument.

One attempted solution to these challenges has been to utilize the trocar as a means for passing the distal end of a percutaneously-inserted instrument back out of a patient's body in order to exchange end effectors. More particularly, an instrument can be percutaneously inserted into, for example, a patient's abdominal cavity, then passed back out of the body through the trocar such that a surgeon or other user can directly manipulate the instrument and any end effector. However, passing the instrument (either with or without an end effector attached) through the trocar in the "wrong" direction (i.e., from its distal end toward its proximal end) can damage the one or more seals present in the trocar that help maintain pneumoperitoneum. This is because trocar seals are often designed with a "duckbill" or other shape that is oriented for proximal-to-distal instrument passage.

Accordingly, there is a need for improved devices and methods that assist users in passing modular end effectors into a patient's body for attachment to a surgical instrument positioned inside the body. There is also a need for such devices and methods that can reduce the number of objects that must be manipulated during such an operation and can reduce the risk of damage to a surgical trocar being used to pass the end effectors into the body.

SUMMARY OF THE INVENTION

The present invention generally provides devices and methods for delivering surgical end effectors into a patient's body for attachment to another surgical instrument in vivo. The devices and methods described herein can reduce the complexity of this type of operation by coupling an end effector loading device to a surgical trocar, for example, in the same manner that an obturator is typically coupled to a trocar. This coupling can effectively combine the loading device and trocar into a single device that is more easily manipulated by a user. The loading device can be configured to selectively couple to an end effector and, upon coupling with a trocar, pass the end effector through a working channel of the trocar for presentation to a surgical instrument positioned near a distal end of the trocar. The loading device can then release the end effector coupled thereto once the end effector is coupled to the surgical instrument. Using the devices and methods described herein, a surgeon or other user can more easily align an end effector and complementary surgical instrument for coupling and can avoid the practice of passing the surgical instrument through the trocar in the "wrong" direction (i.e., from a distal end thereof to a proximal end thereof) in order to attach the end effector to the instrument.

In one aspect, a surgical end effector loading device is provided that can include a housing having a distal-facing first portion configured to couple with a proximal end of a surgical trocar, and an elongate second portion protruding distally from the first portion. The second portion can include a lumen formed therein and can be configured to extend into a working channel of the surgical trocar when the housing is coupled thereto. The device can further include at least one mating element coupled to the housing and configured to interface with a complementary mating element of the surgical trocar to restrict movement of the housing relative to the trocar, as well as an end effector retainer coupled to the housing and configured to selectively couple a surgical end effector to the housing.

The devices and methods described herein can have a number of additional features and/or variations, all of which are within the scope of the present disclosure. In some embodiments, for example, the end effector retainer can be positioned at a distal end of the second portion of the housing, while in other embodiments the end effector retainer can be disposed within the lumen of the housing and can be translatable along a length of the housing. In addition, in some embodiments the device can include an actuator positioned in the housing and coupled to the end effector retainer to selectively release the surgical end effector. The actuator and end effector retainer can have a variety of configurations, but in one embodiment the end effector retainer can include a latch and the actuator can be coupled to the latch by a linkage. In other embodiments, the end effector retainer can include an actuator positioned in the housing and configured to release a surgical end effector from a first, proximal position to a second, distal position relative to the loading device.

In certain embodiments, the at least one mating element can include at least one projection extending from the housing and configured to be received within at least one recess formed in the surgical trocar. However, a variety of other configurations of the at least one mating element are also possible. For example, in some embodiments the at least one mating element can include at least one recess formed in the housing and configured to receive at least one projection formed on the surgical trocar.

Moreover, the at least one mating element can restrict movement of the housing relative to the trocar to a variety of different degrees. For example, in some embodiments the at least one mating element can restrict movement of the housing relative to the surgical trocar in all degrees of freedom. In other embodiments, the at least one mating element can restrict movement of the housing relative to the surgical trocar in at least one degree of freedom and can permit movement of the housing relative to the surgical trocar in at least one other degree of freedom. For example, the housing can be restricted from rotating relative to the trocar, but can be permitted to move axially (e.g., along a longitudinal axis of the trocar) relative thereto.

In certain embodiments, the end effector retainer can include at least one projection configured to be received within at least one recess formed in the surgical end effector. The at least one projection can aid in selectively coupling the end effector to the device. In other embodiments, however, this configuration can be reversed to provide for at least one projection formed on the surgical end effector that is received within at least one recess formed in the end effector retainer.

In other embodiments, the device can further include an advancer slidably disposed within the lumen and configured to translate the surgical end effector along a longitudinal axis of the lumen. Such an advancer can be used to deliver, for example, an end effector positioned within a lumen in the housing of the device through the working channel of a trocar to be received within a patient's body. In some embodiments, the advancer can be coupled to an actuator that extends beyond an outer diameter of the lumen. Such an actuator can be, for example, a button or other component accessible to a user. Moreover, in some embodiments the actuator can be biased radially outward and configured to move into a recess formed in the housing when the advancer is translated to a distal-most position. As a result, the actuator can provide a visual indication of when the end effector is fully deployed. In some embodiments, the visual indication of the extended actuator can be combined with, for example, a colored portion of the actuator that is only visible in the extended position in order to enhance the visual indication to a user. In still other embodiments, different forms of visual indications can be utilized. For example, the housing can include one or more viewports into the lumen to permit visualization of a position of the surgical end effector within the lumen.

In another aspect, a surgical instrument kit is provided that includes a loading device having a housing with at least one mating element coupled thereto, a lumen formed through at least a portion of the housing, and an end effector retainer. The kit can further include a trocar having a proximal end, a distal end, at least one mating element, and a working channel extending therethrough from the proximal end to the distal end, as well as a surgical end effector. Moreover, the surgical instrument end effector can be aligned with the lumen of the loading device and coupled thereto by the end effector retainer, and the housing of the loading device can be coupled to the proximal end of the trocar via the mating elements of the loading device and the trocar.

As with the instrument described above, a number of variations and additional features are possible. For example, in some embodiments the kit can further include an advancer slidably disposed within the lumen of the loading device and configured to translate the surgical instrument end effector along a longitudinal axis of the lumen. Moreover, in some embodiments the kit can also include an actuator coupled to the advancer and configured to indicate when the advancer reaches a distal-most position relative to the lumen of the housing.

In certain embodiments, the kit can further include an actuator positioned in the housing of the loading device and coupled to the end effector retainer to selectively release the surgical end effector. Further, in some embodiments the loading device can include at least one viewport to permit visualization of a position of the surgical end effector within the lumen.

In another aspect, a surgical method is provided that can include coupling a loading device with a surgical trocar such that a lumen formed in the loading device coaxially aligns with a working channel of the surgical trocar and complementary mating features on the loading device and the surgical trocar restrict relative motion therebetween. The method can further include passing an end effector received within the lumen of the loading device through the working channel of the surgical trocar, and selectively releasing the end effector from the lumen of the loading device.

In some embodiments, the method can further include inserting the end effector into the lumen of the loading device. Such a step can include coupling the end effector to the loading device using, for example, an end effector retainer coupled to the loading device.

In some embodiments, the end effector can be coupled to the loading device at a distal end thereof, such that the end effector is passed through the working channel of the trocar when the loading device is coupled to the trocar. In other embodiments, however, the end effector can be translatable within the lumen of the loading device along a longitudinal axis thereof. In such embodiments, the method can further include translating an advancer distally to pass the end effector through the working channel of the surgical trocar.

Further, in some embodiments the step of selectively releasing the end effector from the lumen of the loading device can occur after a surgical instrument couples to the end effector. In such an embodiment, the end effector can be prevented from falling away from the loading device before it is securely attached to another instrument.

In other embodiments, the method can further include coupling an obturator with the surgical trocar such that a shaft of the obturator extends through the working channel and complementary mating features on the obturator and the surgical trocar restrict relative motion therebetween. The method can also include decoupling the obturator from the surgical trocar prior to coupling the loading device with the surgical trocar.

Any of the features or variations described above can be applied to any particular aspect or embodiment of the invention in a number of different combinations. The absence of explicit recitation of any particular combination is due solely to the avoidance of repetition in this summary.

BRIEF DESCRIPTION OF THE DRAWINGS

FIG. 2 is an exploded view of the surgical trocar of FIG. 1A;

FIG. 14B is an alternative perspective view of the assembly of FIG. 14A;

FIG. 5B is an alternative perspective view of the end effector loading device housing of FIG. 15A;

FIG. 20 is an exploded view of the advancer, end effector retainer, and surgical end effector of FIG. 16;

FIG. 25A is a perspective view of the end effector retainer and the end effector of FIG. 16 in an uncoupled configuration;

FIG. 25B is a side view of the end effector retainer and the end effector of FIG. 25A;

FIG. 26A is a perspective view of the end effector retainer and the end effector of FIG. 25A in a coupled configuration;

FIG. 26B is a side view of the end effector retainer and end effector of FIG. 26A;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Further, in the present disclosure, like-numbered components of the embodiments generally have similar features. Still further, sizes and shapes of the devices, and the components thereof, can depend at least on the anatomy of the subject in which the devices will be used, the size and shape of components with which the devices will be used, and the methods and procedures in which the devices will be used.

Surgical devices and methods are described herein that provide for improved delivery of surgical instrument end effectors into a patient's body through a surgical trocar. The devices and methods provided for include features for mating an end effector loading device to a surgical trocar such that a surgeon or other user no longer needs to manipulate two devices separately. Further, certain embodiments can include features to selectively advance an end effector through a trocar working channel after a loading device is coupled thereto, or features to allow an end effector to be rotated, pivoted, or otherwise moved in order to improve alignment with a percutaneously-inserted instrument prior to coupling of the two components. Still further, the devices and methods described herein can include features to selectively release an end effector coupled thereto once a surgical instrument has successfully coupled to the end effector.

Figure 1A:
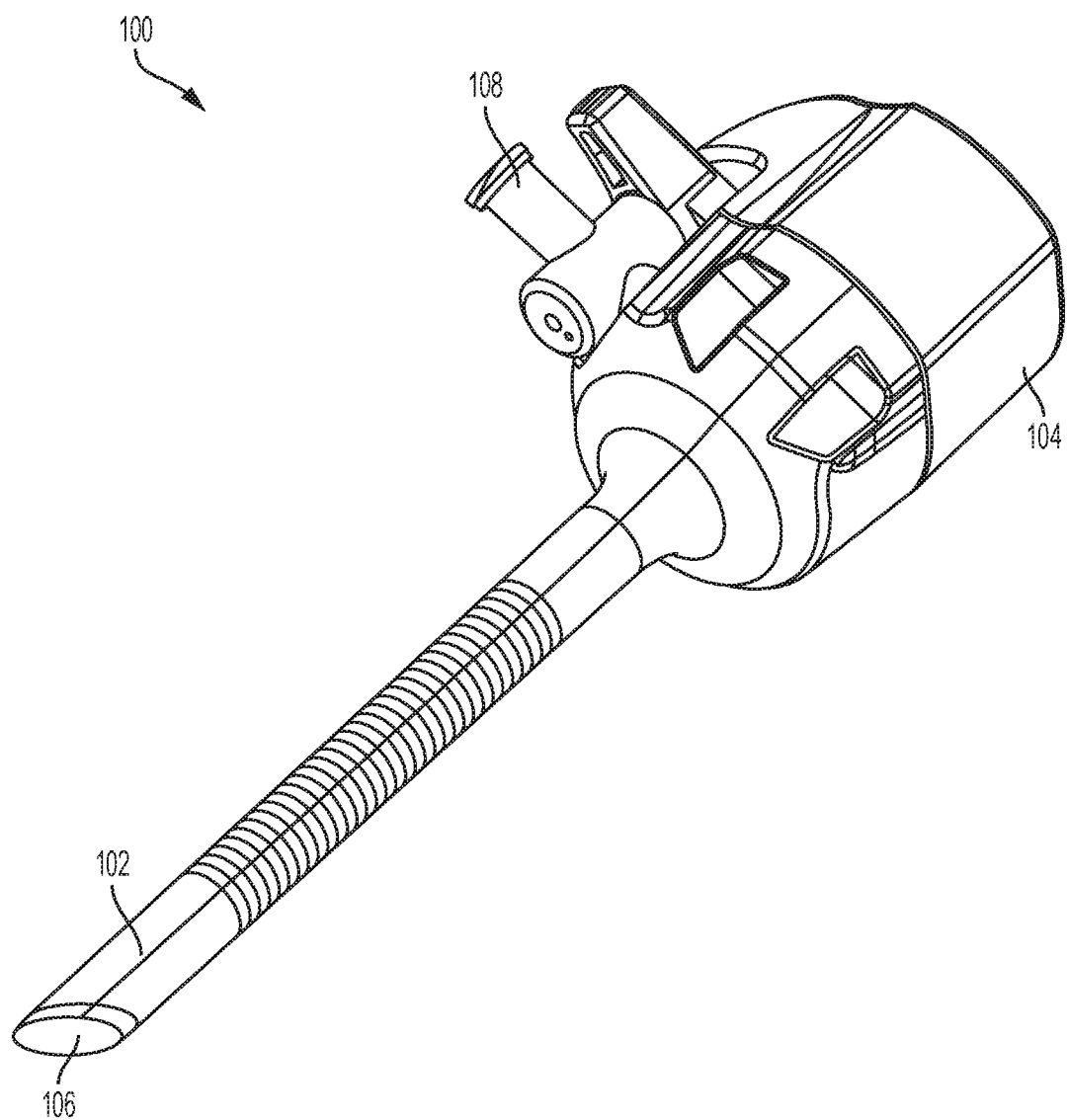
FIG. 1A is a perspective view of one embodiment of a prior art surgical trocar.
Figure 1B:
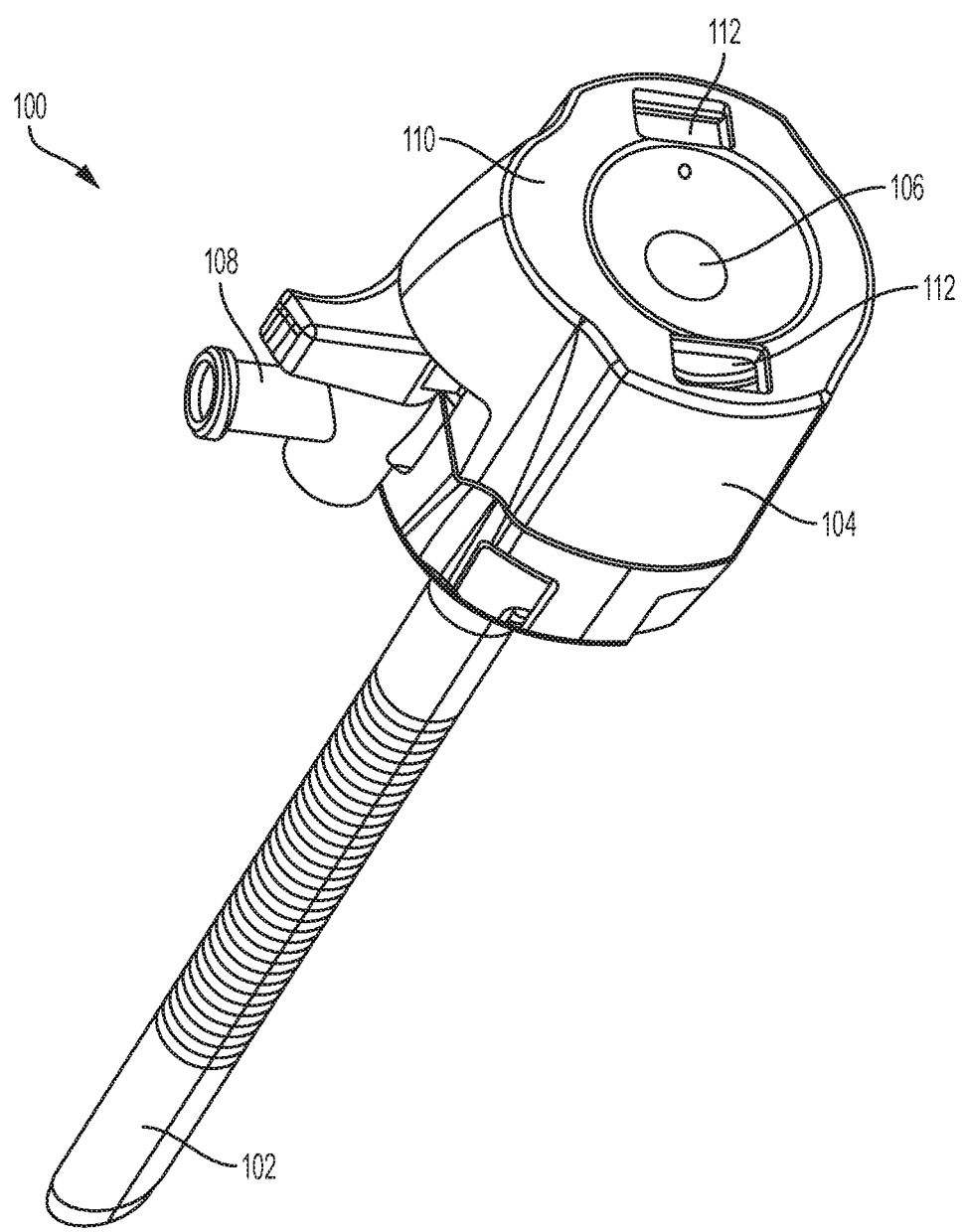
FIG. 1B is an alternative perspective view of the surgical trocar of FIG. 1A.

FIGS. 1A-2 illustrate one embodiment of a surgical trocar 100 known in the art that can be used in connection with the devices and methods described herein. The illustrated trocar 100 is similar to trocars sold under the trade name ENDOPATH XCEL® by Ethicon Endo-Surgery, Inc. of Cincinnati, Ohio, though any other trocar known in the art can also be employed with, or easily adapted to be employed with, the devices and methods described herein. The trocar 100 generally includes a distal trocar sleeve 102 that is coupled to a proximal trocar housing 104. The trocar 100 can have a lumen or working channel 106 extending therethrough and one or more seals (see FIG. 2) can be disposed across the working channel between the distal sleeve 102 and proximal housing 104. Further, an insufflation port 108 can be included to permit the introduction of insufflating gas, such as carbon dioxide, to help maintain pneumoperitoneum during a procedure.

The trocar housing 104 can include a proximal surface 110 configured to couple with, for example, an obturator (not shown) that can be utilized to help pass the trocar 100 through tissue. The trocar housing 104 can also include at least one mating element configured to aid in coupling the obturator to the trocar 100. In the illustrated embodiment, for example, the at least one mating element includes a plurality of recesses 112 configured to receive corresponding protrusions formed on the obturator (not shown). Further details on an exemplary coupling between an obturator and a trocar can be found in U.S. Pat. No. 8,034,032 to Voegele et al., entitled "Multi-Angled Duckbill Seal Assembly," which is hereby incorporated by reference.

Trocars are made in a variety of sizes and are typically denoted by a diameter of the working channel 106. This measure represents the largest width or diameter instrument that can be passed into a patient's body through the trocar. In the case of ENDOPATH XCEL® trocars, for example, the working channel is typically 5 mm or 12 mm in diameter. The smaller of the two sizes is typically utilized to introduce end effectors and other surgical instruments, while a visual scope is often introduced through the larger size working channel. Of course, these are not limitations on the size and intended use of a trocar, but merely examples.

Beyond the basic components described above, the various seals of a trocar are important for maintaining pneumoperitoneum and can be somewhat complex. FIG. 2 illustrates an exploded view of the trocar 100 including its various internal components in this non-limiting exemplary embodiment. From the proximal end of the trocar 100, a first instrument seal 202 is shown. The instrument seal 202 commonly has a round aperture in its center that is coaxially aligned with the working channel 106. The instrument seal 202 is configured to form a seal around, for example, a round-shape scope or instrument being passed through the trocar working channel. In some embodiments, when no instrument is present the aperture can remain open, i.e., it does not completely collapse to seal off proximal and distal portions of the working channel 106.

The instrument seal 202 can be located proximal to a "duckbill" seal 204 that is configured to seal the working channel 106 when no instrument is present. The shape of the duckbill seal 204, having opposed sidewalls that form a straight lip, can be effective to seal the channel in the absence of an instrument, but often fails to form a tight seal around an instrument. This is one reason for including two seals in series that have different shapes and purposes. Of course, a number of other seal shapes, numbers, and configurations are known in the art and can be employed with the devices and methods described herein.

The illustrated trocar 100 also includes an insufflation port valve 206 and inner housing 208 that surrounds the seals 202, 204. Finally, the illustrated embodiment includes a fluid remover assembly formed by a scraper 210 and a sorbent member 212. The fluid remover assembly is configured to remove bodily or other fluids that might be present on an instrument as it is retracted back through the working channel of the trocar proximally. In particular, the scraper 210, which can be formed from a molded polyisoprene and has a central opening coaxially aligned with the working channel 106, presses against an instrument and removes fluid as the instrument is moved relative thereto. The scraper 210 can include a series of radial channels (not shown) formed therein and extending from the central opening. The channels will have a capillary effect and allow fluid to flow radially outward away from the central opening of the scraper 210. This fluid will then be absorbed by the sorbent member 212 that is in contact with an outer portion of the scraper 210. The sorbent member 212 can be formed from, e.g., a polyolefin or other sorbent material.

As noted above, the trocar 100 and other embodiments thereof are often used during minimally invasive procedures to provide a means of accessing the interior of a patient's body. Further, they are commonly used in connection with percutaneously-inserted instruments in order to pass modular end effectors into the patient's body. These end effectors can then be coupled to the narrow distal end of the percutaneous instrument to allow the instrument to perform a variety of tasks. For example, one embodiment of a modular end effector can include a pair of jaws that can be actuated by relative movement of two concentric shafts of a percutaneously-inserted instrument. The shafts can easily be passed through tissue without the use of a trocar or other access device, and the jaws can be coupled thereto in vivo to turn the shafts into a useful tool for grasping and manipulating tissue.

Challenges with using these types of instruments typically arise in connection with the process of coupling, decoupling, or exchanging the modular end effectors with the distal end of the percutaneously-inserted instrument. The process typically involves a separate loading device that grasps the end effector and is used to introduce the end effector into the patient's body by passing it through the working channel of the trocar 100. The loading device and instrument must then be properly aligned to insert the shaft of the instrument into a socket formed in the end effector. Completing this coupling process can require manipulating the loading device, the trocar it is passed through, and the percutaneously-inserted instrument simultaneously.

To simplify this process, some surgeons and other users opt to pass the percutaneously-inserted instrument back out of the body through the trocar 100. This allows the surgeon to directly manipulate the end effector and distal end of the instrument. However, passing the instrument through the trocar 100 from its distal end to its proximal end can damage the trocar seals. As shown in FIG. 2, the trocar seals (as well as the fluid removal assembly if present) are designed to accept instruments moving in a proximal-to-distal direction. Retraction of instruments initially passed in this manner is not problematic because the instrument shaft maintains the seal in an open position and prevents inadvertent deformation of the seals during proximal retraction. When an instrument is initially passed in a distal-to-proximal direction, however, the instrument can deform or destroy the trocar seals 202, 204.

Figure 3A:
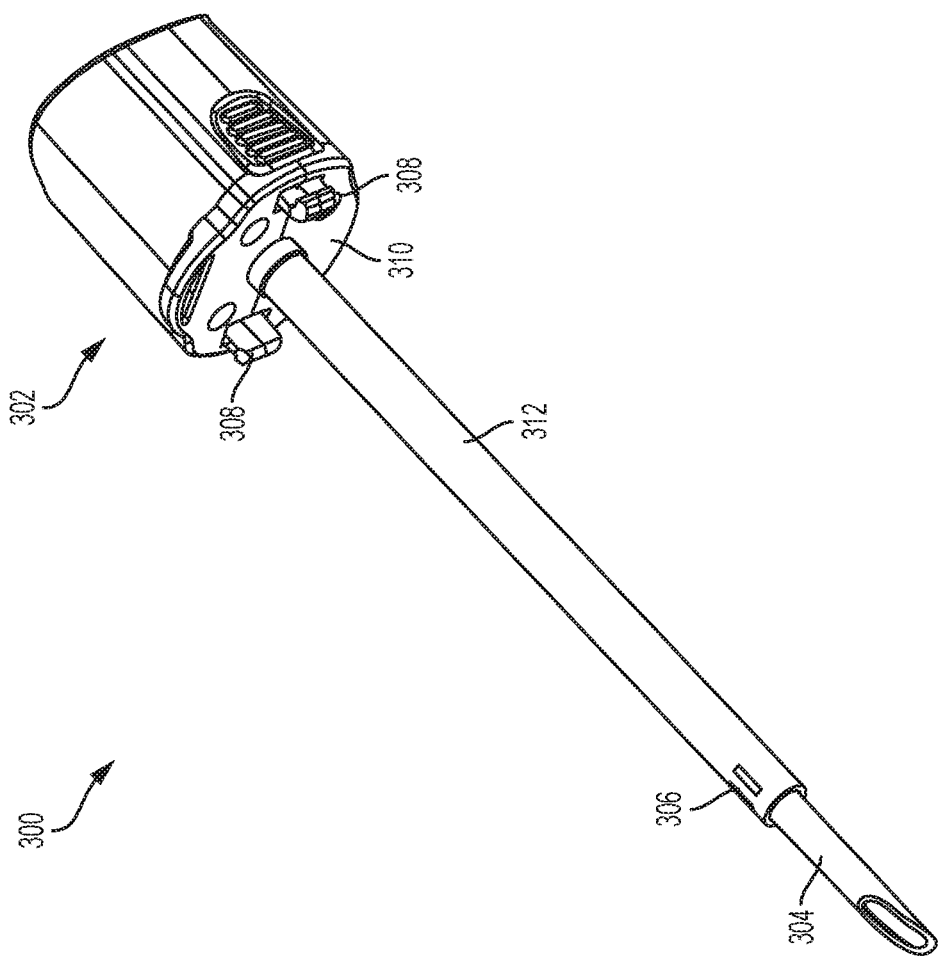
FIG. 3A is a perspective view of one embodiment of a surgical end effector loading device.
Figure 3B:
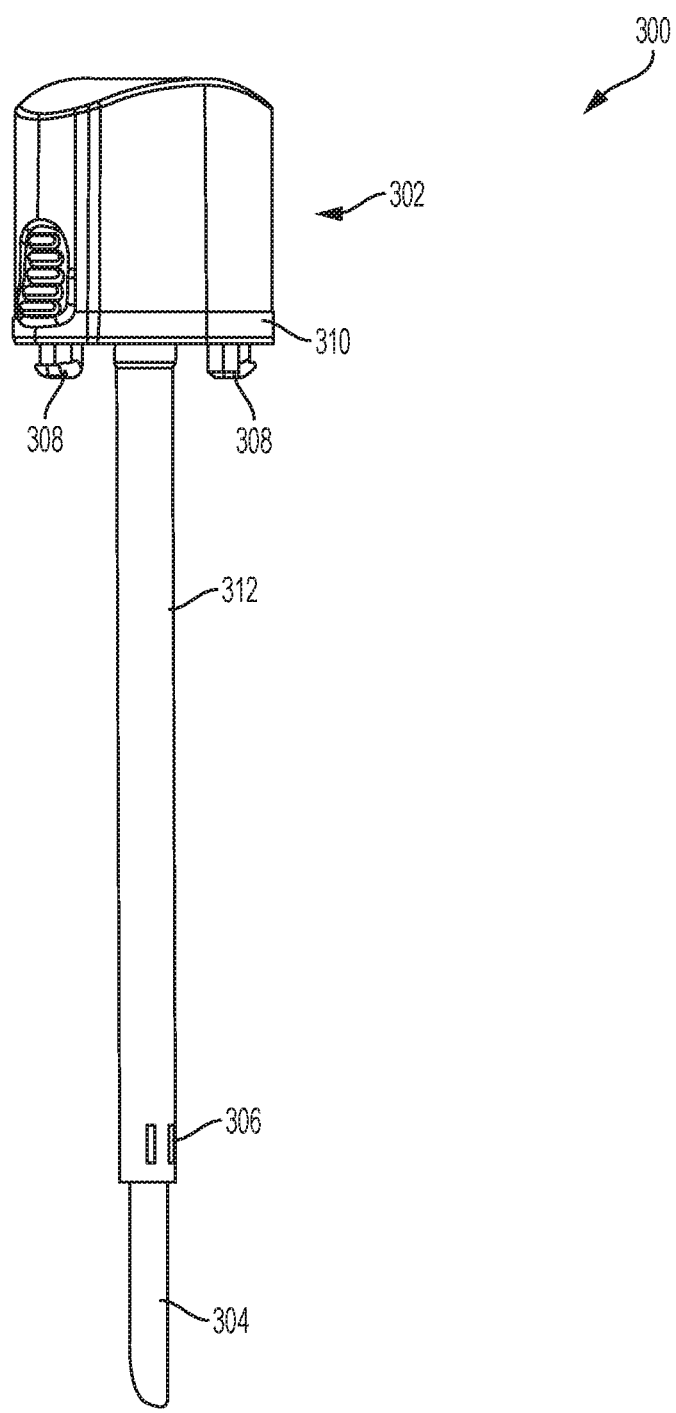
FIG. 3B is an alternative perspective view of the device of FIG. 3A.
Figure 4:
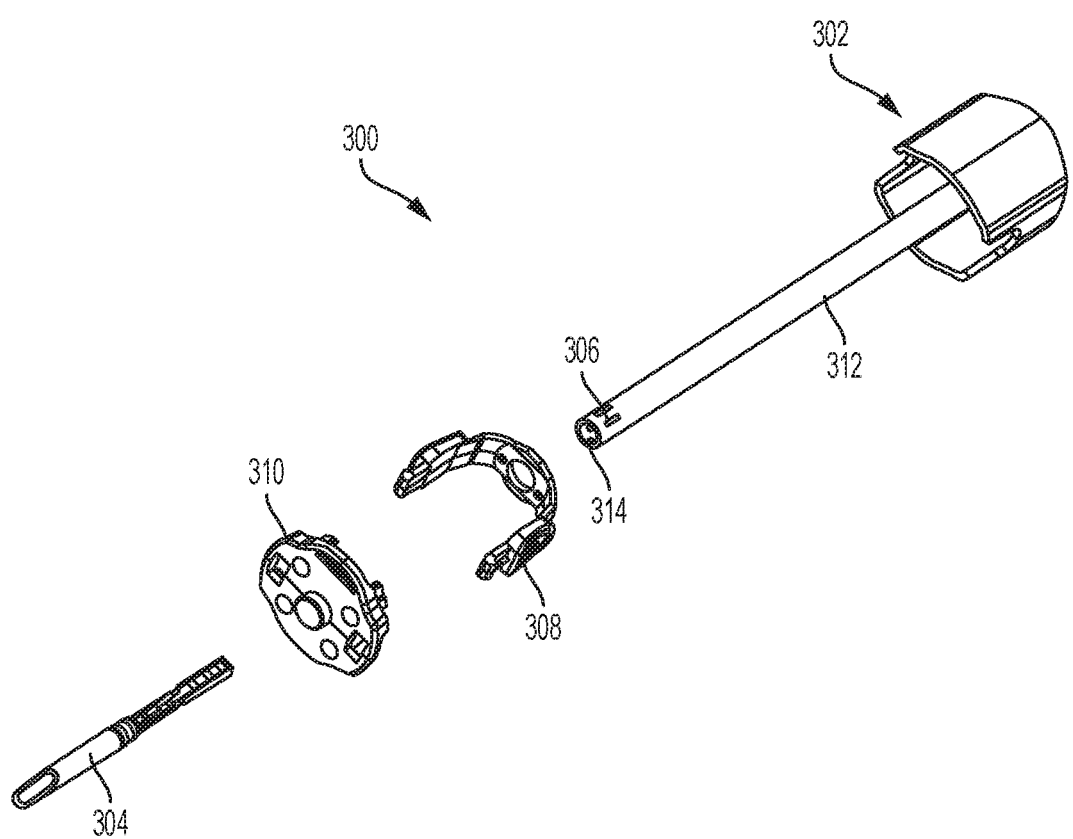
FIG. 4 is an exploded view of the device of FIG. 3A.

FIG. 3A-4 illustrate one embodiment of a surgical end effector loading device 300 that addresses these and other challenges. The device 300 generally includes a housing 302 with a lumen formed therein that can receive a surgical instrument end effector 304, sometime referred to as an end effector assembly. The device also includes an end effector retainer 306 that can selectively couple the surgical end effector to the housing and release it when desired (e.g., once the end effector has been successfully coupled to a percutaneously-inserted instrument). Moreover, the device 300 can include at least one mating element 308 that is coupled to the housing 302 and configured to interface with a complementary mating element of a surgical trocar (e.g., mating elements 112 of trocar 100) to restrict movement of the housing relative to the trocar.

More specifically, and as shown in the exploded view of FIG. 4, the housing 302 can include a distal-facing first portion 310 that is configured to couple with a proximal end 110 of a trocar 100. The housing can further include an elongate second portion 312 that protrudes distally from the first portion 310 and includes a lumen 314 formed therein that is configured to extend into a working channel 106 of a trocar 100. The lumen 314 can be sized to receive the surgical end effector 304 therewithin. Further, an end effector retainer 306, can be formed in a sidewall of the lumen 314 (or otherwise coupled to the lumen) in order to selectively couple the end effector 304 to the device 300. Finally, the housing 302 can include at least one mating element 308, shown in FIG. 4 as a single resilient U-shaped component having distal hooks for engaging with the plurality of recesses 112 formed in the proximal surface 110 of the trocar 100.

Figure 5A:
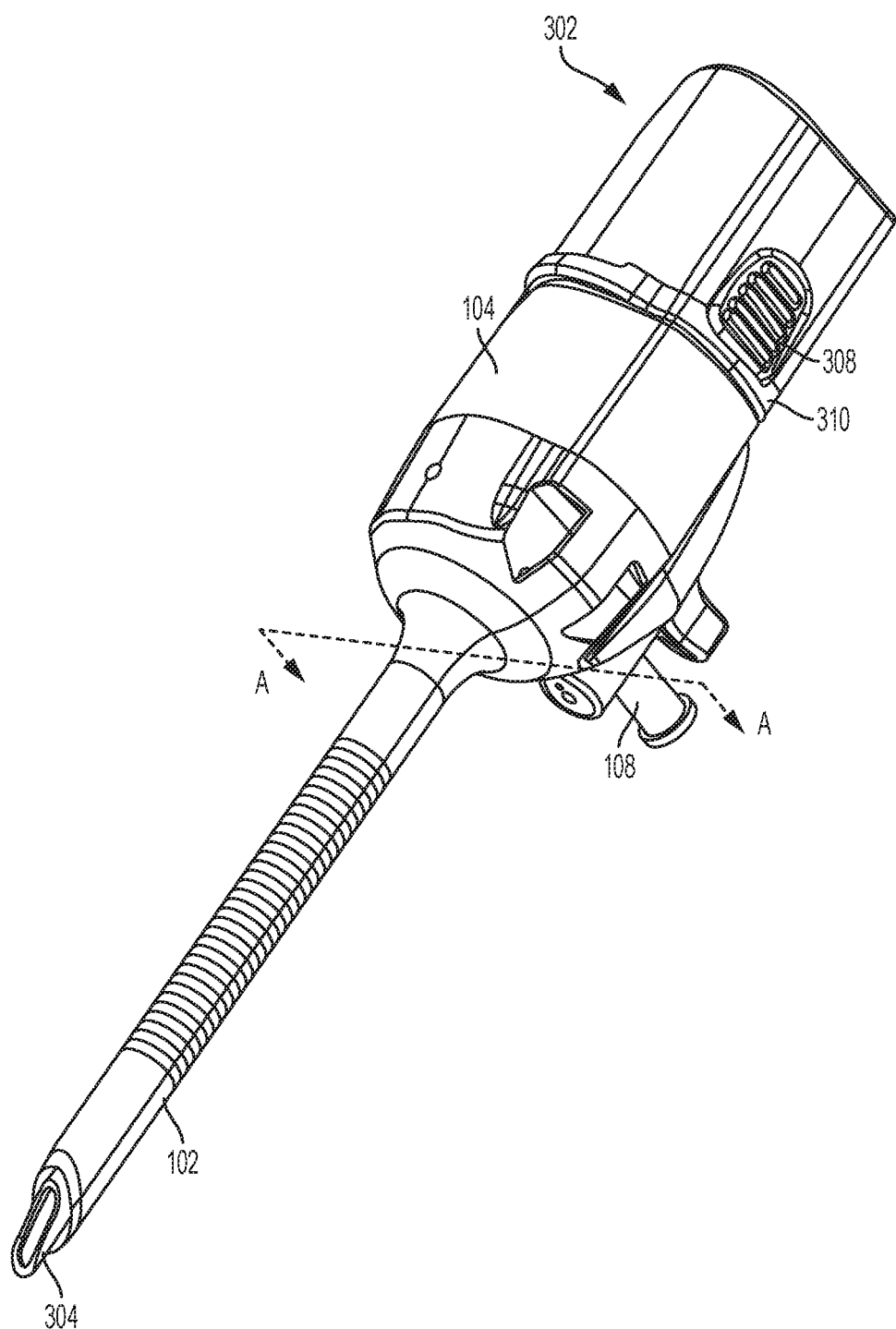
FIG. 5A is a perspective view of an assembly that includes the device of FIG. 3A coupled to the trocar of FIG. 1A.
Figure 5B:
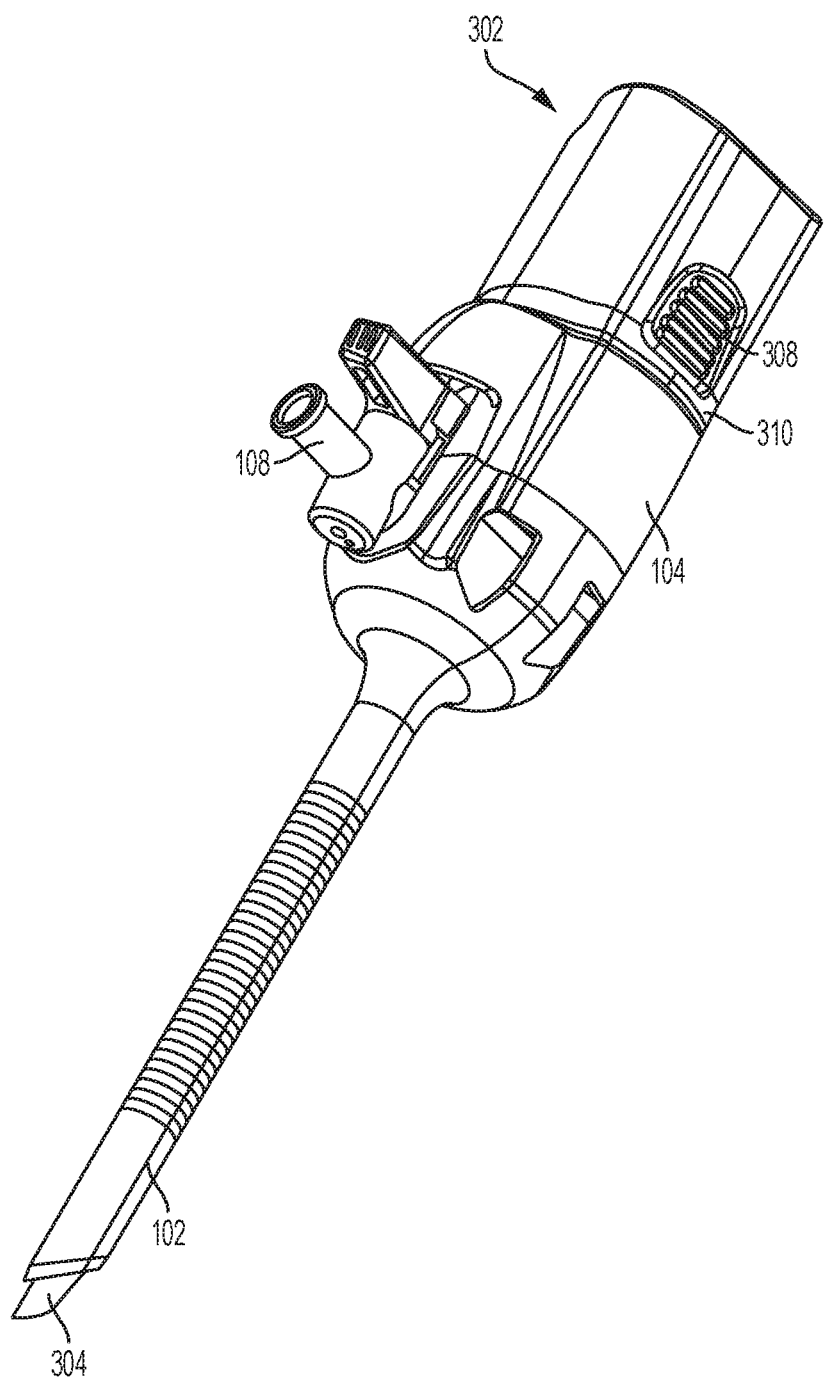
FIG. 5B is an alternative perspective view of the assembly of FIG. 5A.

FIGS. 5A and 5B illustrate alternative views of the loading device 300 coupled to the trocar 100. As shown in the figures, the distal-facing first portion 310 of the housing 302 can abut against the proximal surface 110 of the trocar 100. Further, the elongate second portion 312 can extend through the working channel 106 of the trocar 100 such that a surgical end effector 304 attached to the elongate second portion extends out of a distal end of the trocar sleeve 102.

Figure 6:
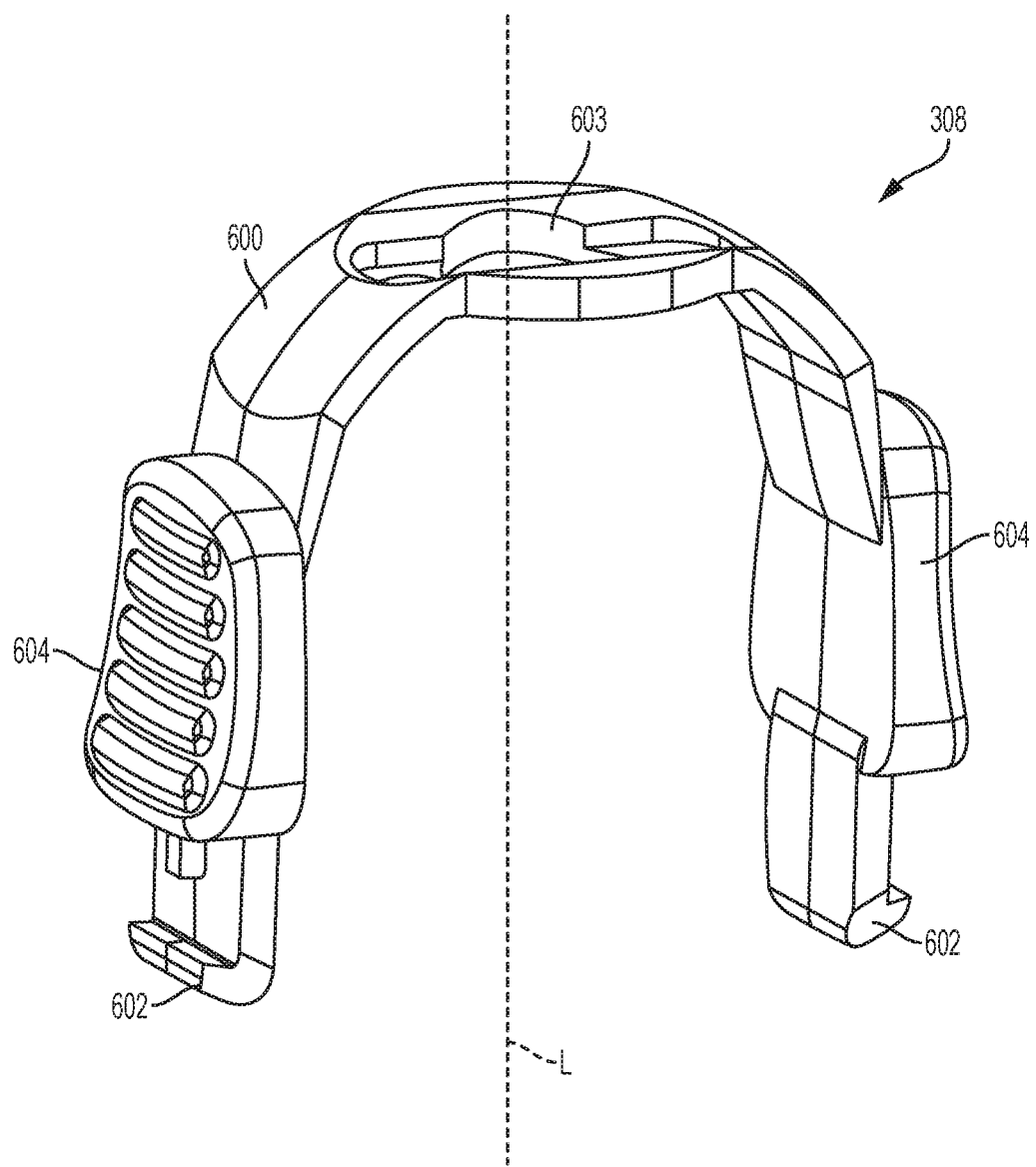
FIG. 6 is a perspective view of one embodiment of a mating element of the surgical end effector loading device of FIG. 4.
Figure 7:
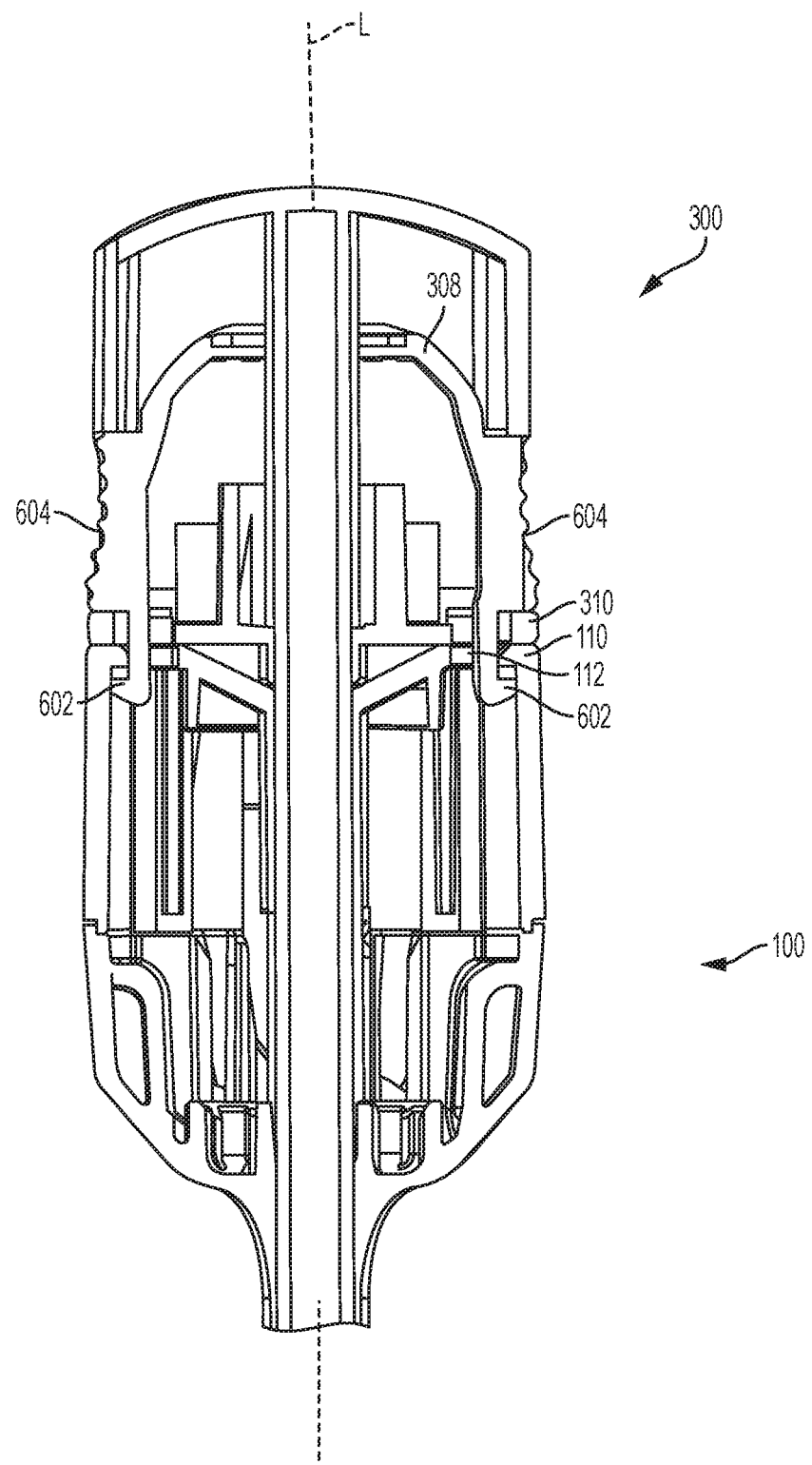
FIG. 7 is a side cross-sectional view of the assembly of FIG. 5A taken along the line A-A.
Figure 8:
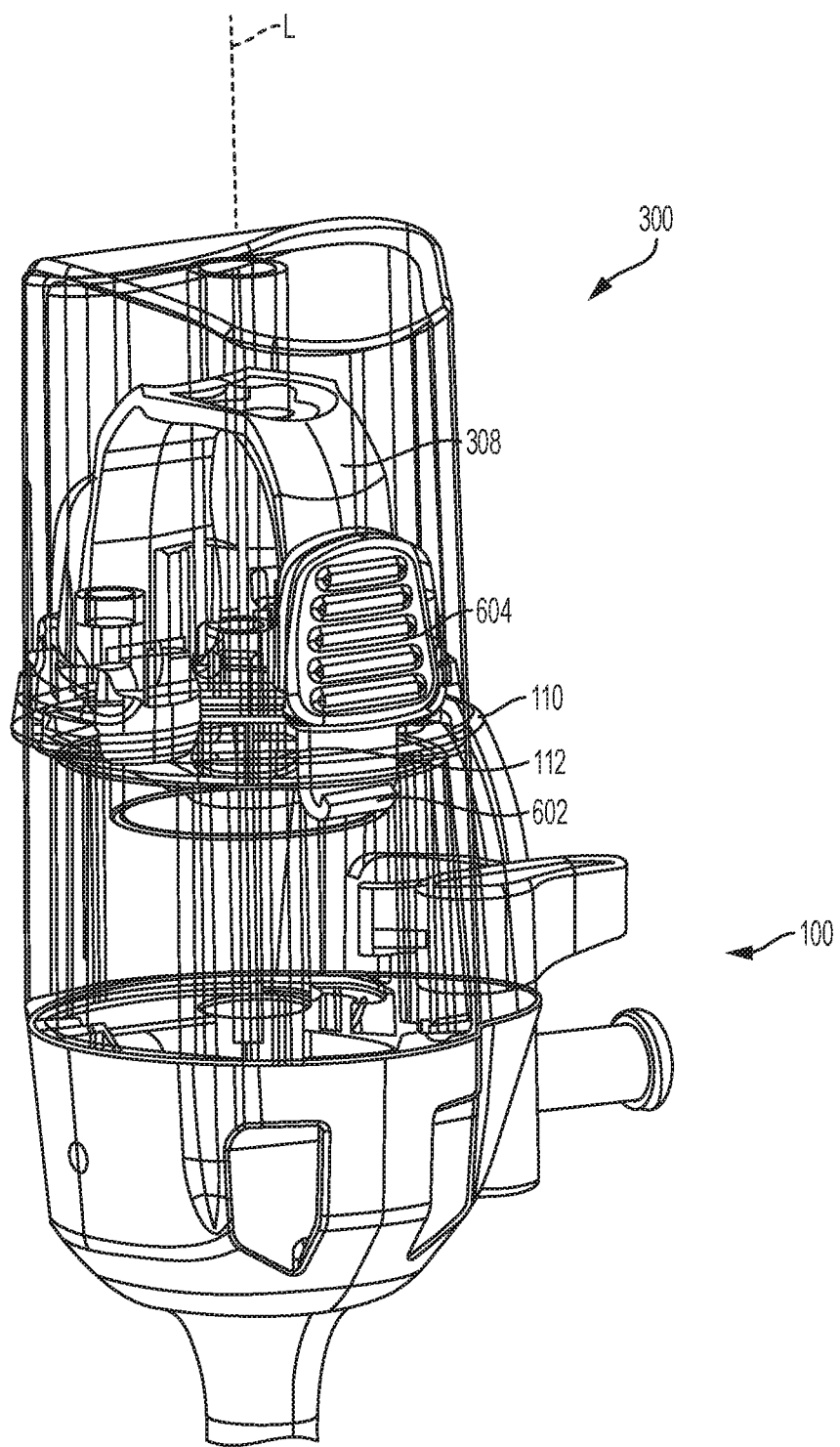
FIG. 8 is a partially-transparent perspective view of the assembly of FIG. 5A.

The loading device 300 can be coupled to the trocar 100 via one or more mating elements formed on the device that interface with complementary mating elements formed on the trocar. FIGS. 6-8 illustrate the coupling between the loading device 300 and the trocar 100 in more detail. As shown in the detail view of the mating element 308 in FIG. 6, the mating element can be in the form of a U-shaped frame 600 having hooks, barbs, or clips 602 formed on distal ends thereof. The U-shaped frame 600 can also include a central lumen 603 formed therein that is configured to receive the elongate second portion 312 of the housing 302. The mating element 308 can be formed from a resilient material, such as an elastically deformable polymer or metal, and can be biased away from a longitudinal axis L. This biasing can aid the mating element 308 in interfacing with a recess formed in the trocar 100. The mating element 308 can also include opposed actuating surfaces 604 that can be depressed by a surgeon or other user in order to selectively decouple or release the loading device 300 from the trocar 100 when desired. The actuating surfaces 604 can include ridges or other surface features formed thereon to aid a user in grasping and depressing them. While the mating element 308 is illustrated as a single U-shaped frame 600 with opposed distal end features 602, in other embodiments a plurality of separate mating elements can be employed at various positions around the elongate second portion 312 that is configured to extend into a working channel of the surgical trocar 100, or a differently-shaped frame can be employed, e.g., a T-shaped or cross-shaped frame having four distal mating features.

FIGS. 7 and 8 show cross-sectional and partially transparent views, respectively, of the loading device 300 when coupled to the trocar 100. These views highlight the interaction between the mating element 308 of the loading device 300 and the complementary mating elements 112 of the trocar 100. In particular, the hooks 602 formed at the distal ends of the U-shaped mating element 308 extend into the recesses 112 formed in the proximal surface 110 of the trocar 100. Further, due to the outward bias of the mating element 308, the hooks 602 engage an underside of the proximal surface 110 of the trocar 100 and prevent the loading device 300 from being drawn away from the trocar axially (i.e., along a longitudinal axis L). In addition, the generally rectangular cross-sectional shape of the mating element 308 can substantially fill the generally rectangular recesses 112, thereby preventing the loading device 300 from rotating or otherwise moving radially relative to the longitudinal axis L. Accordingly, the mating element 308 of the loading device 300 can be configured to restrict movement of the loading device 300 relative to the trocar 100 in all degrees of freedom.

To release the loading device 300 from the trocar 100 (e.g., at the conclusion of a surgical procedure, or if a different loading device with a different surgical end effector is to be passed through the trocar working channel 106), a surgeon or other user can depress the opposed actuating surfaces 604 of the mating element 308 in order to move the distal hooks 602 against any biasing force towards the longitudinal axis L. This movement of the hooks 602 can allow the hooks to disengage from the underside of the proximal surface 110 of the trocar 100 and pass through the recesses 112 formed therein. Accordingly, the loading device 300 can be selectively coupled to the trocar 100.

The illustrated mating element 308 is just one embodiment of a mating element, however, and a variety of other configurations are also possible. For example, the configuration of distally-protruding hooks 602 on the loading device 300 and recesses 112 formed in the trocar 100 can be reversed such that hooks protruding from the trocar proximal surface can be received within recesses formed in a distal-facing portion 310 of the loading device housing 302. In still other embodiments, the bias and orientation of the hooks 602 can be reversed such that they are biased radially inward toward a longitudinal axis L, rather than radially outward as shown. Moreover, the hooks 602 can be positioned on an outer surface of the loading device 300 and configured to engage with recesses, shelves, or other surface features formed on an outer surface of a proximal portion of the trocar 100. There are a variety of other known coupling mechanisms in the art that can also be employed. Regardless of the particular configuration of the mating elements, the loading device 300 can include at least one mating element that is complementary to at least one mating element formed on the trocar 100. In many cases, the at least one mating element on the trocar can be pre-existing and utilized to attach other trocar accessories, such as an obturator.

Still further, certain embodiments of the at least one mating element 308 can be configured to permit at least some relative movement between the loading device 300 and the trocar 100. For example, in some embodiments the at least one mating element 308 can include at least one cylindrical rod or other projection that extends into a recess formed in the trocar 100 without utilizing a hook or other feature to positively latch on to the trocar. In such an embodiment, the loading device 300 can be prevented from moving radially with respect to, or rotating about, a longitudinal axis L, but can be permitted to move axially relative to the longitudinal axis L. In still other embodiments, a distal-facing portion 310 of the loading device housing 302 can include an outer wall configured to extend over a proximal portion of the trocar 100, and one or more splines can be formed on both the loading device 300 and trocar 100 to prevent relative rotation or radial movement with respect to the longitudinal axis L. In still other embodiments, rotation about the longitudinal axis L can be permitted while movement in other directions can be restricted. Of course, any combination of various mating elements can be utilized as known in the art, and need not conform to the specific examples provided herein.

Figure 9:
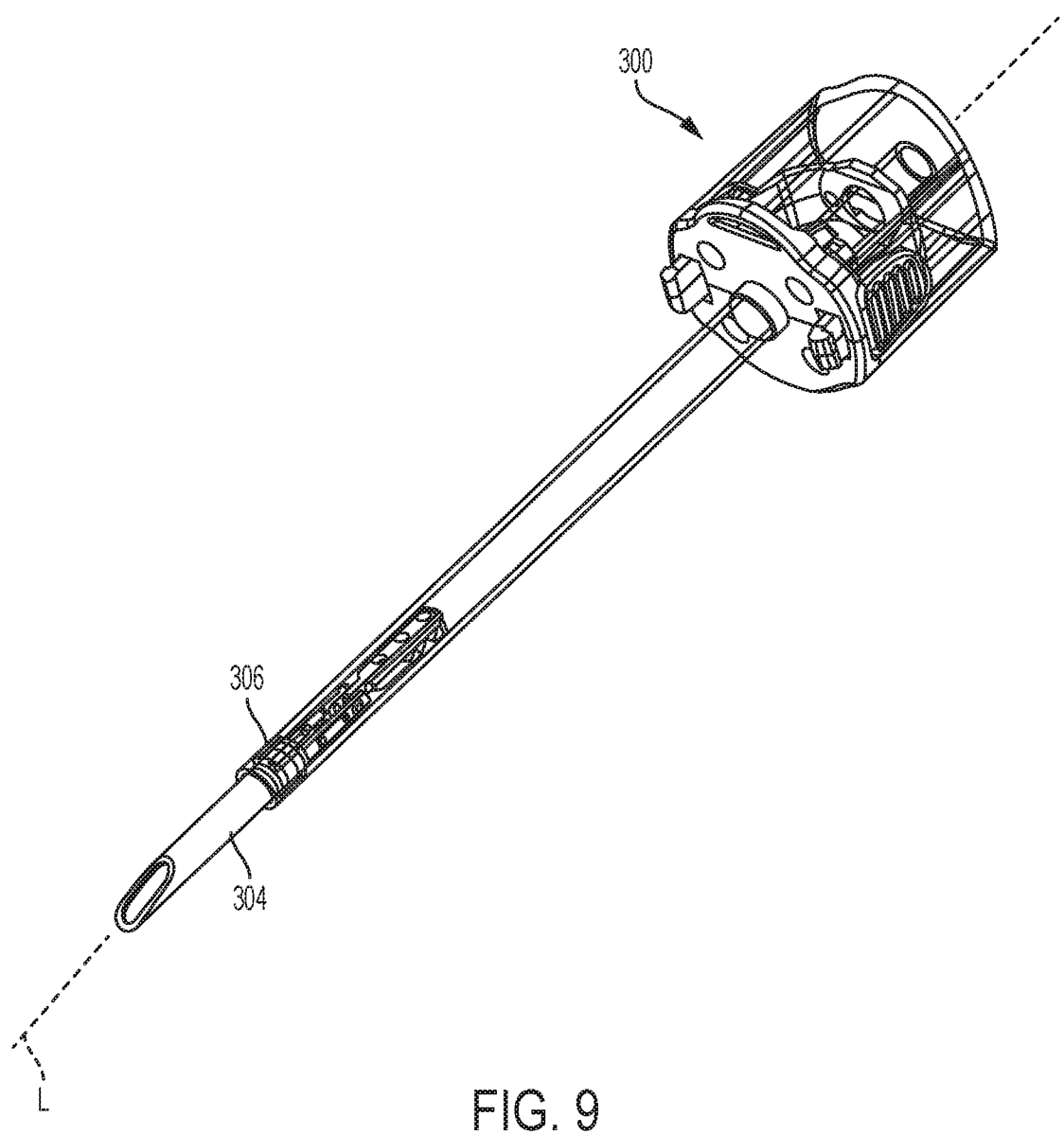
FIG. 9 is a partially-transparent perspective view of the device of FIG. 3A.
Figure 10:
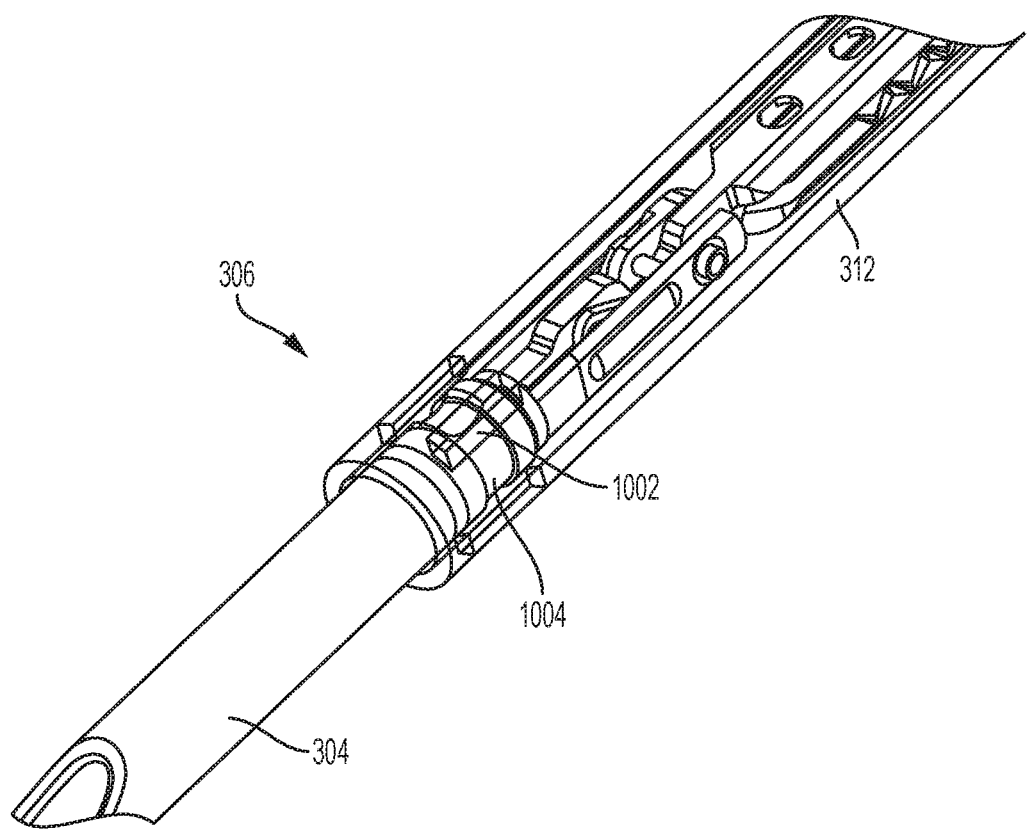
FIG. 10 is a partially-transparent detail view of a distal portion of the device of FIG. 3A.
Figure 11:
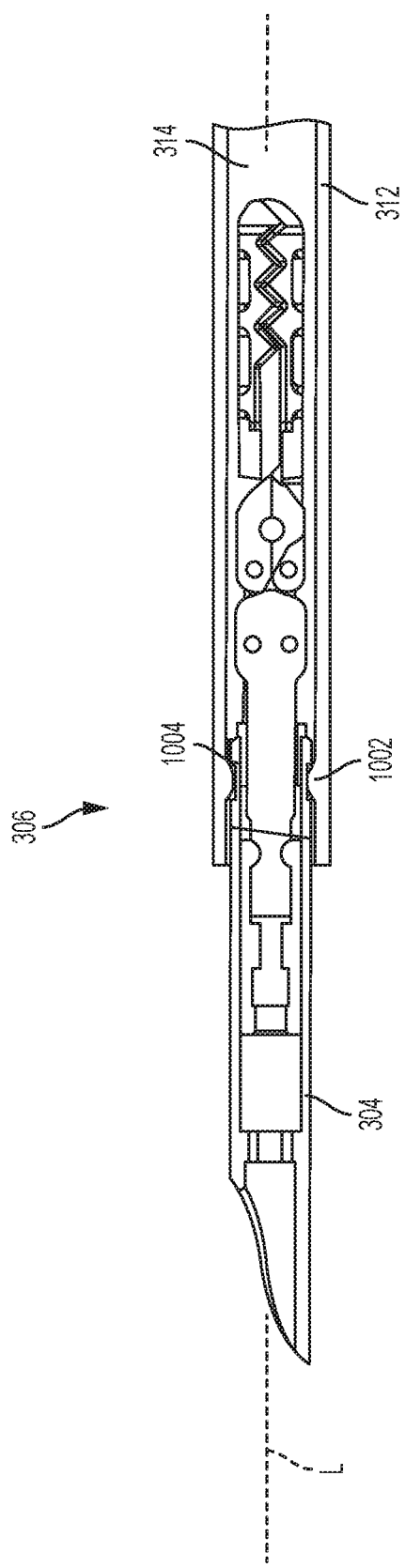
FIG. 11 is a side cross-sectional view of a distal portion of the device of FIG. 3A.

FIGS. 9-11 illustrate the end effector retainer 306 of the loading device 300 in greater detail. The end effector retainer 306 can have a number of different configurations capable of selectively coupling a surgical end effector 304 to the loading device 300 for delivery through the working channel 106 of the trocar 100. In the illustrated embodiment, the end effector retainer 306 includes at least one projection 1002 that is configured to extend into at least one recess 1004 formed in the end effector 304. As shown in FIG. 10, the recess 1004 can be, for example, an annular recess formed around the circumference of the end effector 304 along a length thereof. The at least one projection 1002 can be resiliently biased such that, when an end effector 304 is loaded into the lumen 314 of the loading device 300, the at least one projection 1002 can be pushed radially outward relative to a longitudinal axis L. When the end effector 304 is pushed into the lumen 314 far enough that the recess 1004 aligns with the at least one projection 1002, the at least one projection can be biased radially inward relative to the longitudinal axis L in order to restrict further motion of the end effector 304 relative to the loading device 300.

The illustrated end effector retainer 306 is just one possible embodiment and a number of variations or alternatives can be employed. For example, the illustrated configuration can be reversed to provide an end effector 304 having radially-outward-biased protrusions formed thereon that are configured to fit into recesses formed on an inner sidewall of the lumen 314. Alternatively, any of a variety of other latching mechanisms can be utilized to couple the end effector 304 to the loading device 300. Certain embodiments of an end effector retainer 306 can allow for rotation of the end effector 304 when coupled (and permit coupling of the end effector in any rotational orientation), such as the illustrated annular recess 1004, or can prevent such rotation (e.g., if separate hemispherical recesses were employed in place of the annular recess 1004). Still other possible embodiments of an end effector retainer are described in more detail below.

Figure 12A:
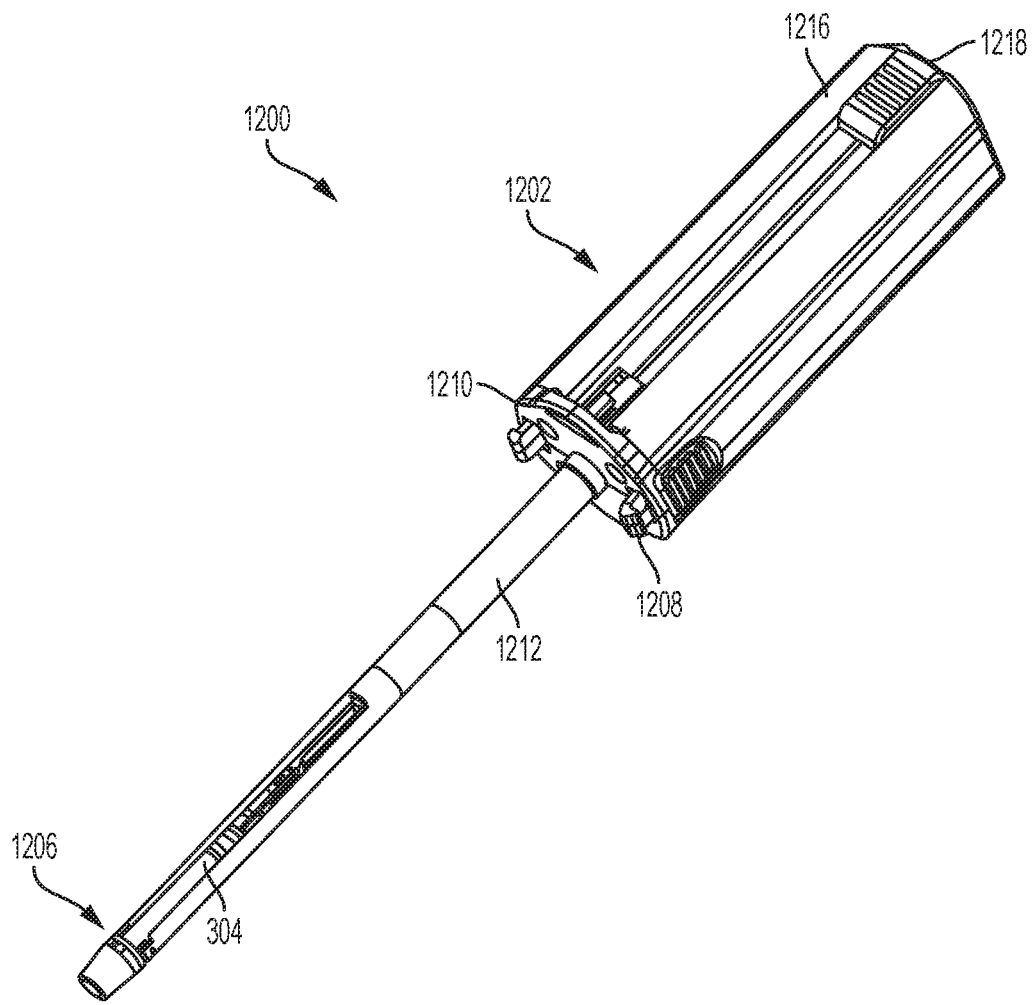
FIG. 12A is a perspective view of another embodiment of a surgical end effector loading device.
Figure 12B:
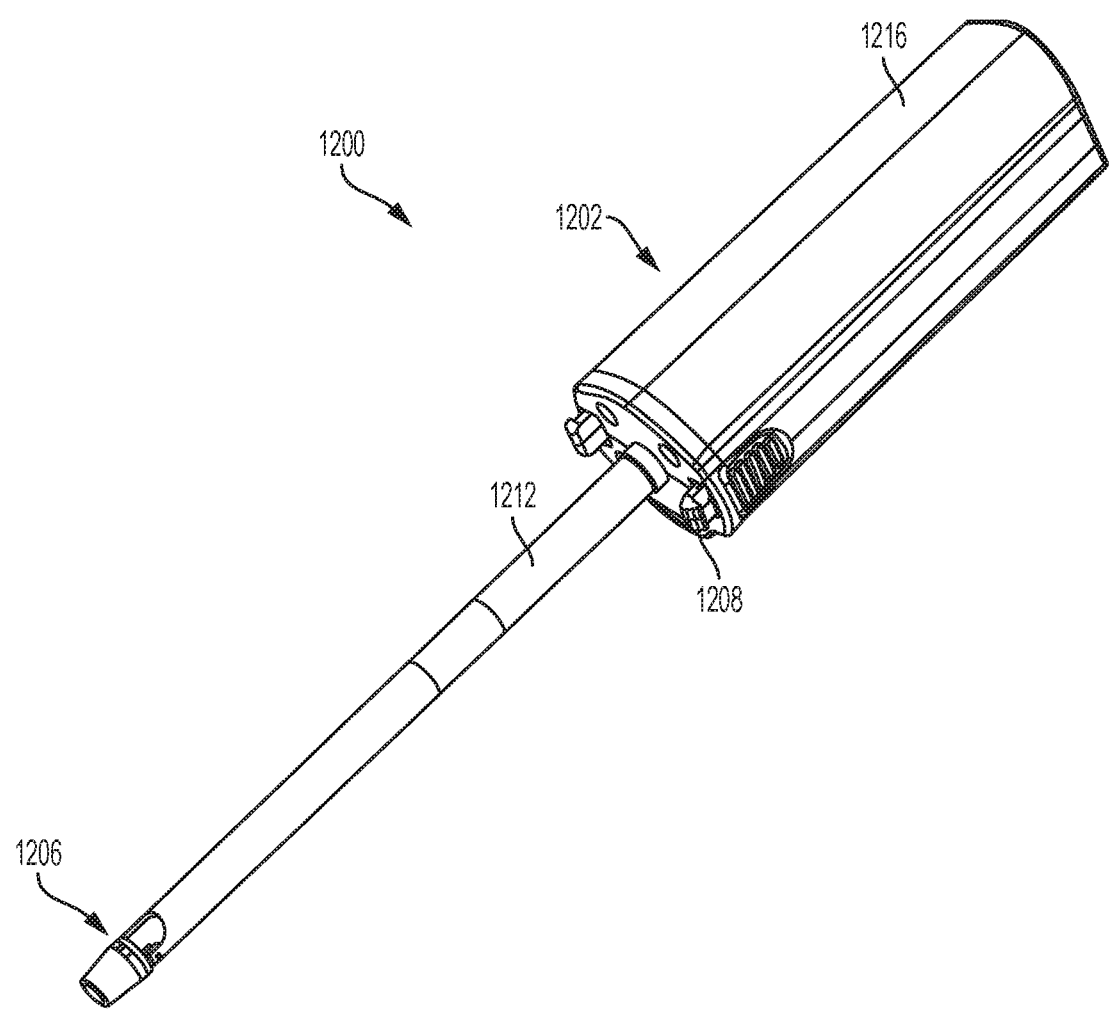
FIG. 12B is an alternative perspective view of the device of FIG. 12A.
Figure 13:
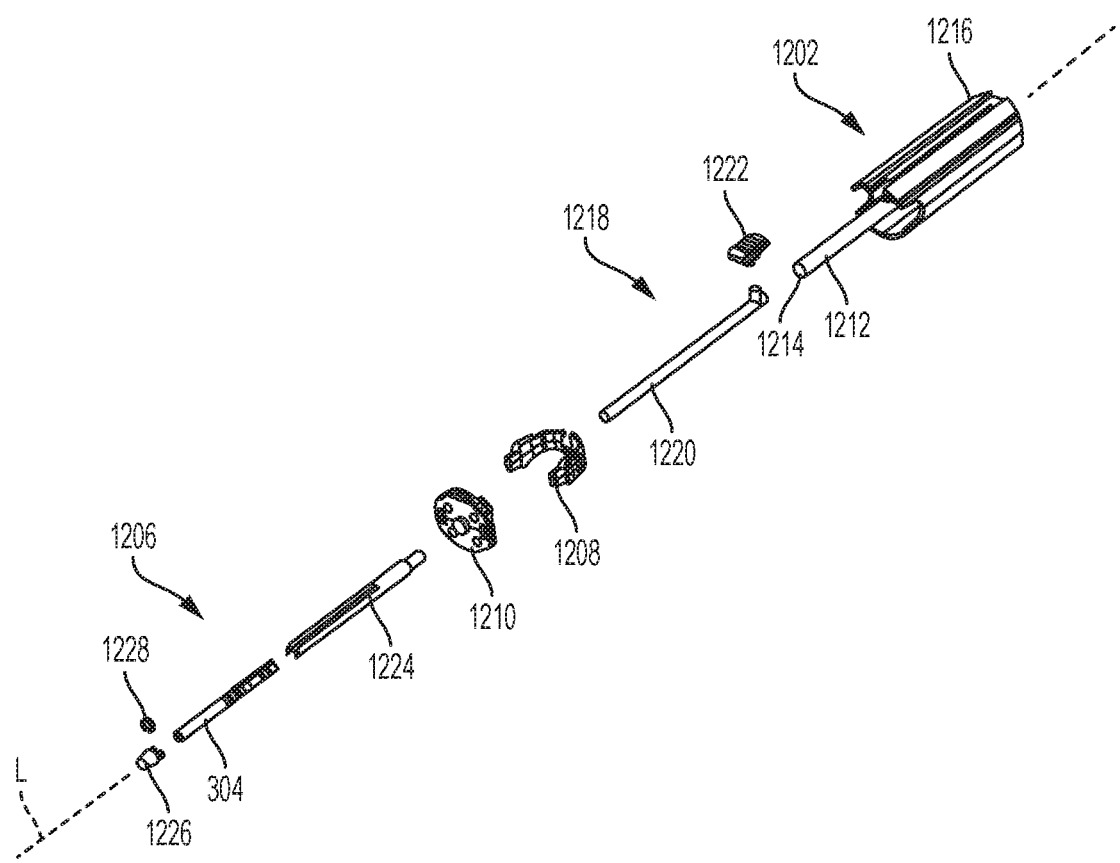
FIG. 13 is an exploded view of the device of FIG. 12A.

FIGS. 12A-13 illustrate another embodiment of a loading device 1200 configured to couple with the trocar 100 and deliver an end effector 304 through a working channel 106 thereof. Similar to the loading device 300 discussed above, the loading device 1200 includes a housing 1202, end effector retainer 1206, and at least one mating element 1208. The housing 1202 of the device 1200 also includes a first distal-facing portion 1210 configured to interface with a proximal portion of the trocar 100, and a second elongate portion 1212 that protrudes distally from the first portion 1210 and is configured to be received within a working channel 106 of the trocar 100. In contrast to the loading device 300, however, the device 1200 is configured to selectively translate the end effector 304 proximally and distally along a length thereof. As a result, the housing 1202 includes an advancer 1218 that can be utilized to translate the end effector 304 and end effector retainer 1206, as well as an extended proximal portion 1216 that can accommodate the advancer.

More particularly, and with reference to the exploded view of FIG. 13, the device 1200 includes a housing 1202 having a proximal portion 1216 and elongate distal portion 1212, as well as a distal-facing portion 1210 configured to abut against a proximal surface 110 of the trocar 100. The housing also includes a lumen 1214 formed therein that houses the advancer 1218. The advancer 1218 can include a plunger component 1220 disposed within the lumen 1214 and an actuating component 1222 that can extend out of the lumen and be manipulated by a surgeon or other user. In addition, the housing can include at least one mating element 1208 that is similar to the mating element 308 described above. The plunger component 1220 can interface with a proximal end of the end effector retainer 1206 to control its position along a length the longitudinal axis L of the device 1200. The end effector retainer 1206 can include a housing 1224, a pivoting end cap 1226, and a retention clip 1228. Further details on these components are provided below.

Figure 14A:
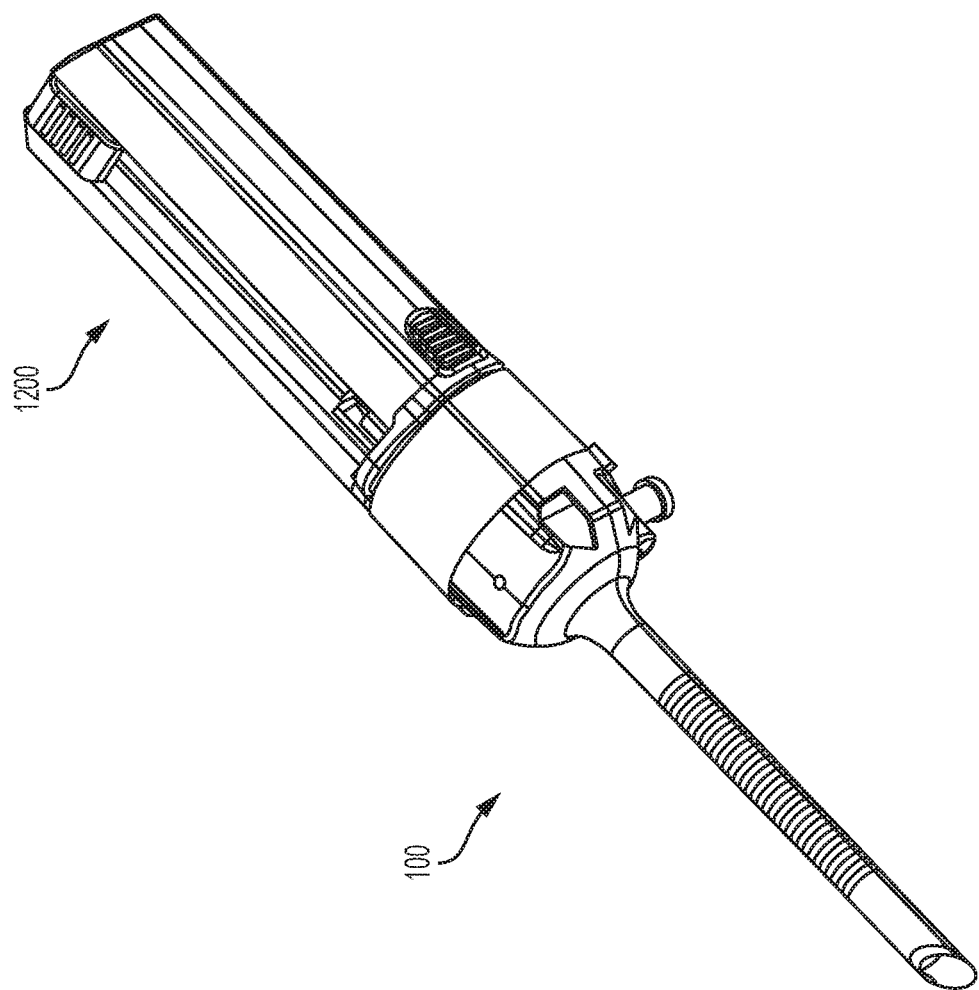
FIG. 14A is a perspective view of an assembly that includes the device of FIG. 12A coupled to the trocar of FIG. 1A.

FIGS. 14A and 14B illustrate alternative views of the loading device 1200 when coupled to the trocar 100. Note that the advancer 1218 of the loading device 1200 is retracted to a proximal-most position and, as a result, the end effector 304 is not extending from a distal end of the trocar 100, in contrast to the embodiment shown in FIGS. 5A and 5B. The loading device 1200 can selectively couple with the trocar 100 in the same manner as the loading device 300 described above. For example, the at least one mating element 1208 can include opposed outwardly-biased hooks or other projections that extend into complementary recesses 112 formed in a proximal surface 110 of the trocar 100 and latch onto an underside of the proximal surface of the trocar to restrict relative movement of the loading device and the trocar. Further, any of the variations or alternative mating element configurations described above can be utilized in connection with the loading device 1200.

Figure 15A:
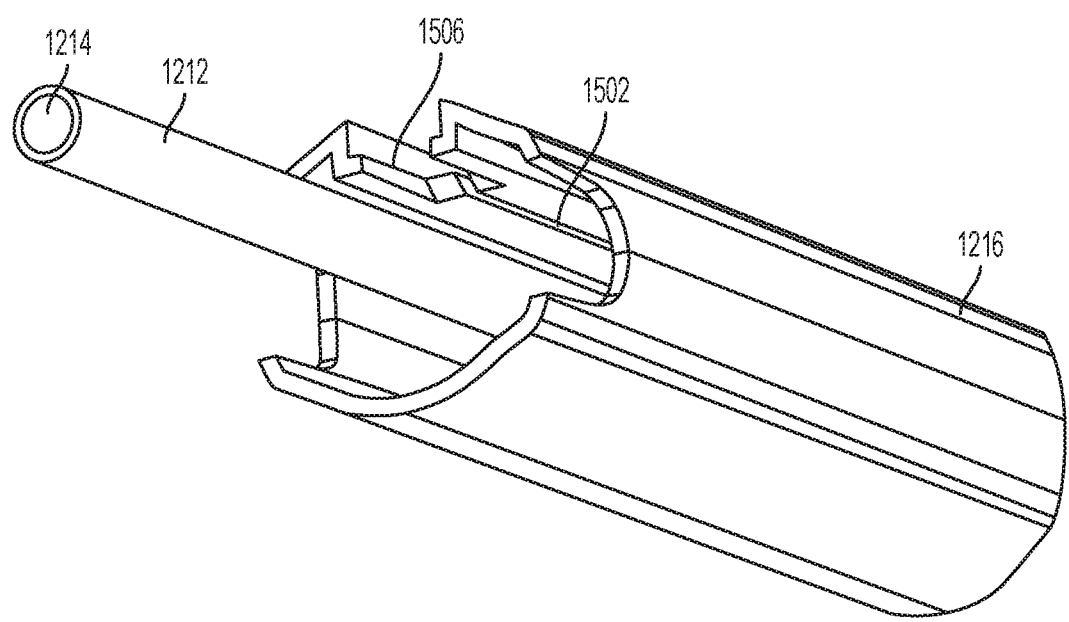
FIG. 15A is a perspective view of an end effector loading device housing of the end effector loading device of FIG. 12A.
Figure 15B:
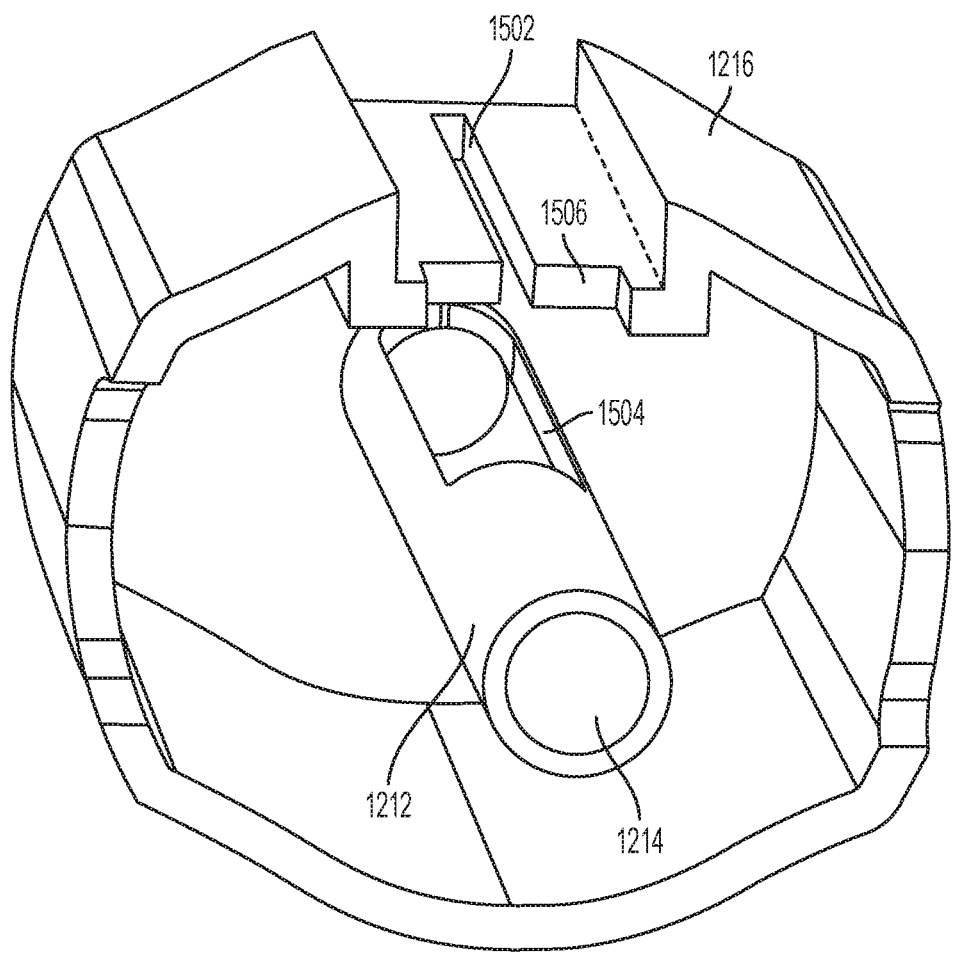

FIGS. 15A and 15B illustrate alternative views of a portion of the housing 1202 of the device 1200. In particular, these figures illustrate a longitudinal slot 1502 formed in the proximal portion 1216 of the housing to accommodate the advancer 1218 and its longitudinal movement relative to the housing 1202. In addition, a cut-out 1504 is formed in the elongate portion 1212 of the housing 1202 to similarly accommodate the advancer 1218 and, more specifically, the actuating component 1222 that extends out from the plunger component 1220 that is disposed within the lumen 1214 of the housing. Moreover, the slot 1502 terminates at a distal end thereof in a larger recess 1506 that allows the actuating component 1222 to extend outward when a distal-most position is reaches, as explained in more detail below. While not shown in the figure, the housing 1202 can also include one or more viewports formed therein (e.g., in the form of cut-outs similar to cut-out 1504, or portions formed from transparent materials) to permit visualization of a position of the surgical end effector within the lumen 1214. Such a viewport can provide a user with another form of feedback to confirm the status of an end effector coupled to the loading device.

Figure 16:
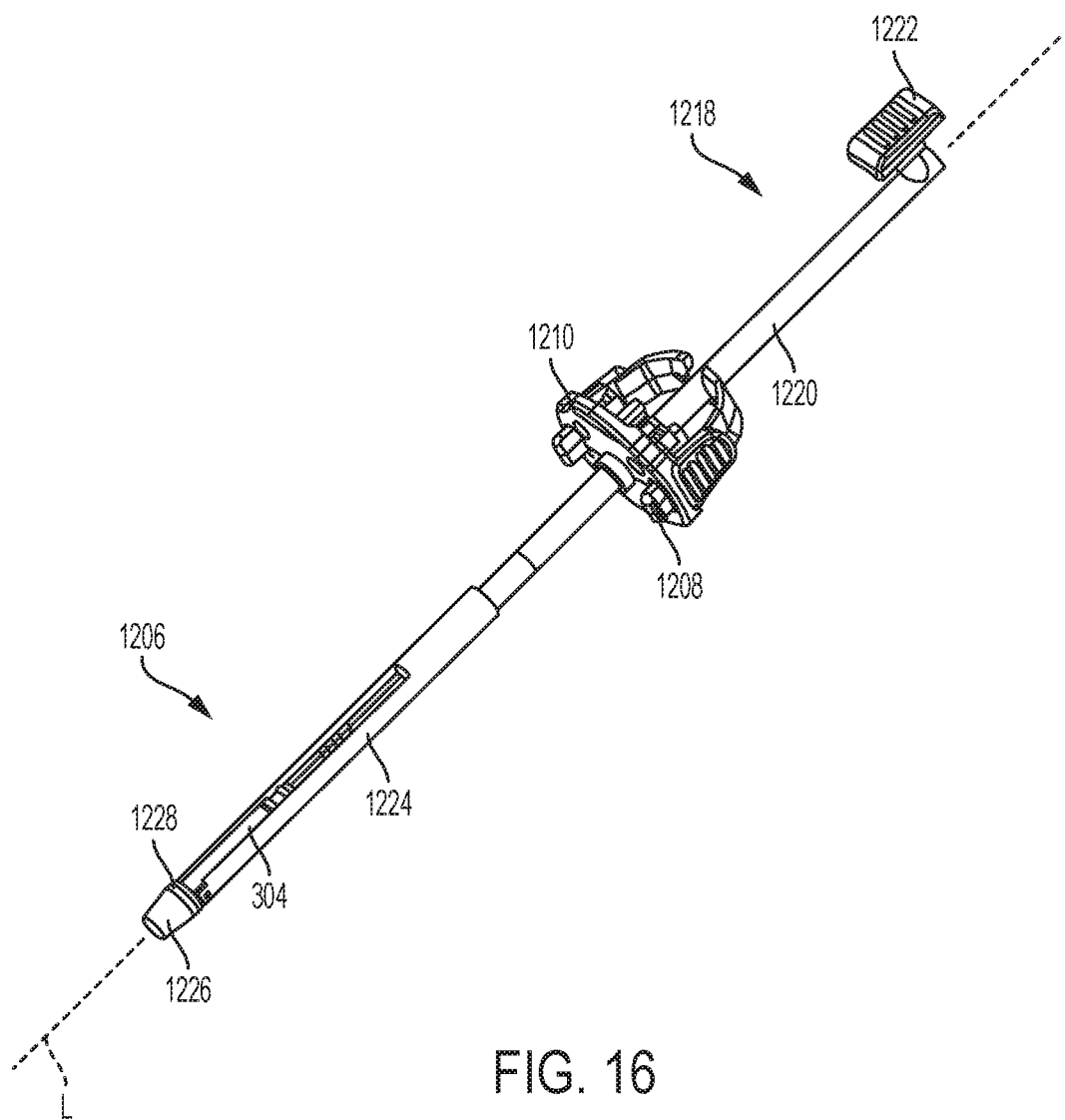
FIG. 16 is a perspective view of some of the components of the device of FIG. 12A including an advancer, an associated actuator, a mating element, an end effector retainer, and a surgical end effector.

FIGS. 16-19 illustrate the various components that enable selective translation of the end effector 304 along a longitudinal axis L of the loading device 1200. FIG. 16 illustrates the loading device 1200 without the proximal portion 1216 or elongate portion 1212 of the housing 1202. In this view the configuration of the advancer 1218 and end effector retainer 1206 are visible. More particularly, a distal end of the plunger component 1220 of the advancer 1218 can be coupled to a proximal end of the end effector retainer housing 1224. As a result, any longitudinal movement of the advancer 1218, e.g., movement effected by a surgeon manipulating the actuating component 1222, can be directly transferred to the end effector retainer 1206. In some embodiments the coupling of the plunger component 1220 and end effector retainer housing 1224 can be rigid, while in other embodiments the end effector carrier can be permitted to rotate relative to the plunger component 1220.

Figure 17:
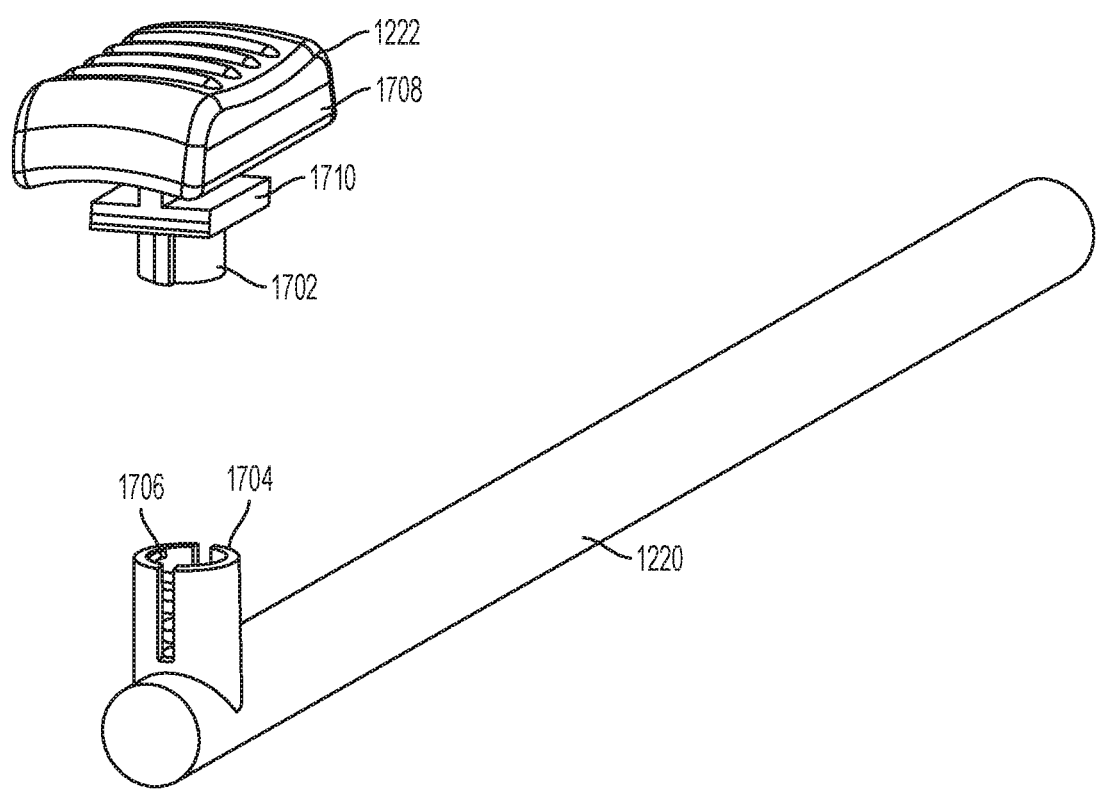
FIG. 17 is a perspective view of the advancer and associated actuator.

As shown in FIG. 17, the plunger component 1220 of the advancer 1218 can be coupled to the actuating component 1222 by fitting a projection 1702 formed on the actuating component into a recess 1704 formed in the plunger component. Further, the actuating component can be biased away from the plunger component (i.e., biased radially outward relative to the longitudinal axis L), for example using a spring 1706 seated within the recess 1704.

Figure 18A:
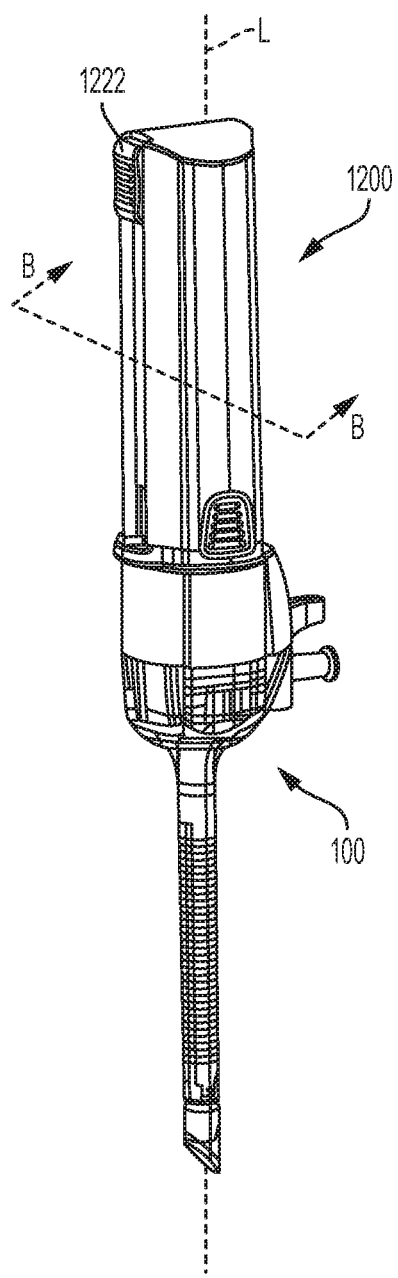
FIG. 18A is a perspective view of the device of FIG. 12A in a first, retracted configuration.
Figure 18B:
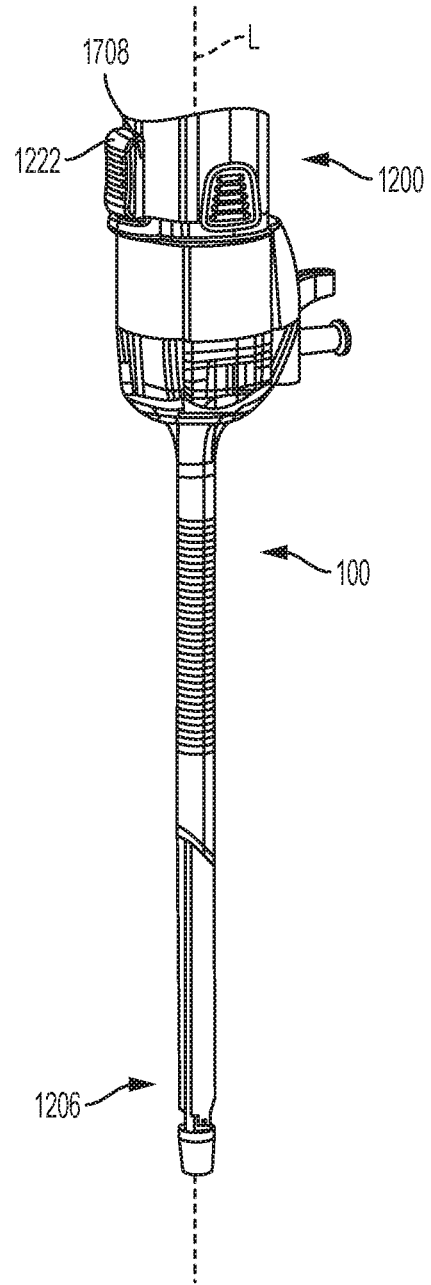
FIG. 18B is a perspective view of the device of FIG. 12A in a second, deployed configuration.

FIGS. 18A and 18B illustrate the loading device 1200 coupled to the trocar 100 and disposed in proximally retracted and distally extended configurations, respectively. In the proximally retracted configuration of FIG. 18A, the actuating component 1222 of the advancer 1218 is positioned at a proximal end of the slot 1502 formed in the housing of the device 1200 and the distal end of the device 1200 is disposed proximal to a distal end of the trocar 100. In the distally extended configuration of FIG. 18B, in contrast, the actuating component 1222 of the advancer 1218 is positioned at a distal-most end of the slot 1502 and the end effector retainer 1206 is extending distally beyond the distal end of the trocar 100.

Figure 19:
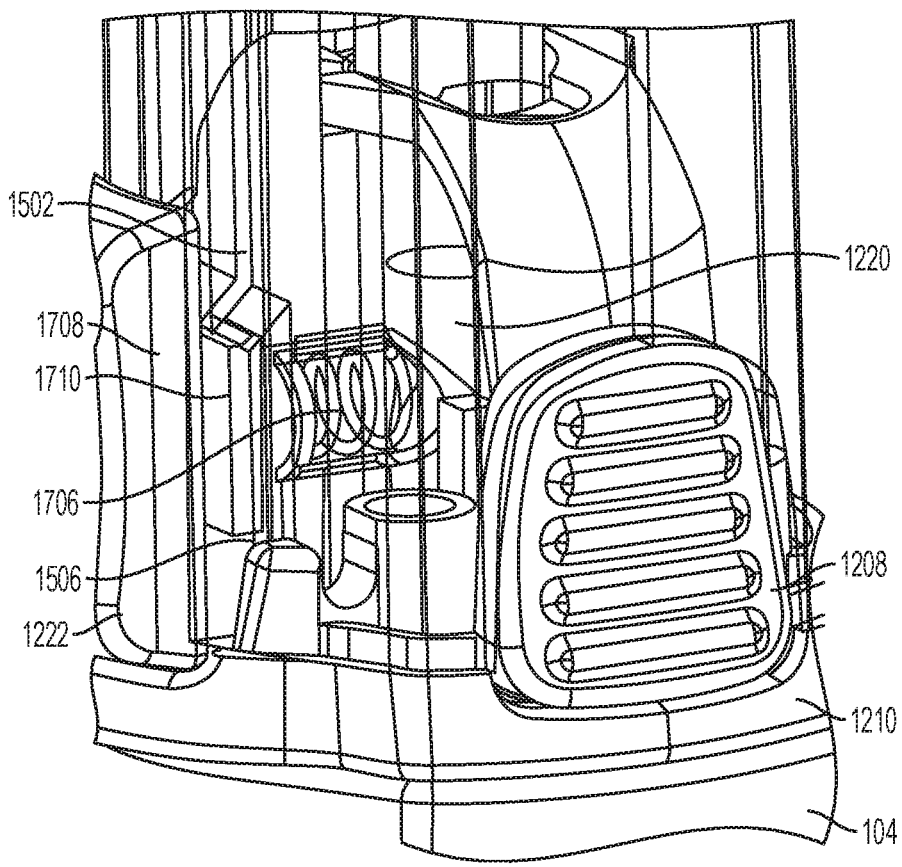
FIG. 19 is a partially-transparent detail view of the device of FIG. 12A with an advancer in a distal-most position.

Moreover, the actuating component 1222 is extending radially outward in FIG. 18B farther than it is in FIG. 18A. This further extension is the result of the actuating component 1222 being aligned with the recess 1506 disposed at a distal end of the slot 1502 formed in the housing 1202, such that the biasing force from the spring 1706 urges the actuating component 1222 radially outward from the longitudinal axis L, as shown in FIG. 19. This additional movement of the actuating component 1222 upon reaching a distal-most position of the advancer 1218 can serve to visually indicate to a user that the end effector is in a fully deployed position. For example, the actuating component 1222 can include a portion 1708 having a color different from other portions of the component. This alternative color portion 1708 can be positioned such that it is visible only when the actuating component 1222 is extended radially outward at a distal-most end of the slot 1502.

The radially-outward movement of the actuating component 1222 at a distal-most position of the advancer 1218 can also be utilized to lock the advancer against inadvertent proximal retraction. For example, the actuating component 1222 can include a plate 1710 that is configured to ride just radially inward from the slot 1502 when the advancer is proximal of the recess 1506 formed in the housing 1202. When the advancer 1218 reaches the distal end of the slot 1502, however, the plate 1710 can move radially outward into the recess 1506 due to the biasing force of the spring 1706, as shown in FIG. 19. The plate 1710 can then abut against a proximal surface of the recess 1506 and prevent the advancer from being retracted proximally unless a user first depresses the actuating component 1222 radially inward against the biasing force of the spring 1706.

FIGS. 20-26 illustrate the end effector retainer 1206 in more detail. As noted above, the end effector retainer 1206 can be disposed at a distal end of the plunger component 1220 of the advancer 1218 and can be configured to selectively couple to an end effector 304. The end effector retainer can include a housing 1224, as well as a pivoting end cap 1226 and retention clip 1228. The illustrated end effector retainer 1206 can ease the process of aligning an end effector with a percutaneously-inserted surgical instrument by allowing the end effector to pivot relative to the retainer, in contrast to, for example, the end effector retainer 306 that requires an instrument to align with a longitudinal axis L of the loading device 300.

Figure 21A:
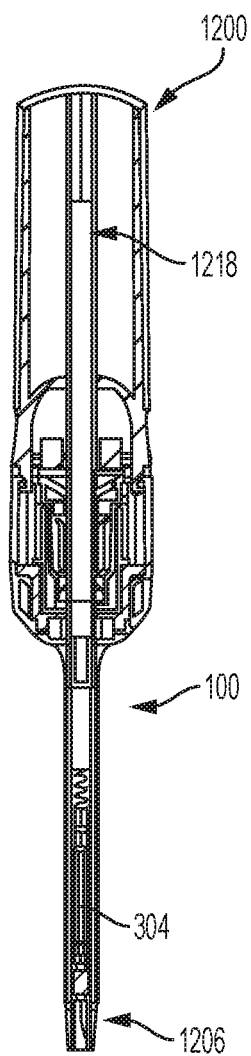
FIG. 21A is a side cross-sectional view of the device of FIG. 18A taken along the line B-B in the first, retracted configuration.
Figure 21B:
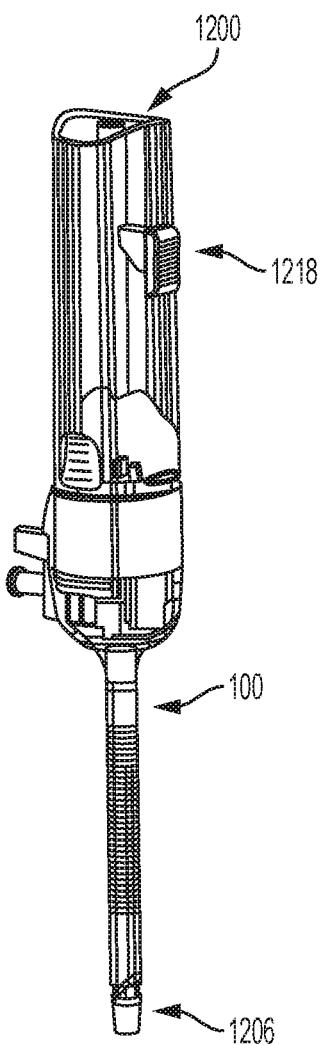
FIG. 21B is a perspective view of the device of FIG. 18A moving from the first, retracted configuration towards the second, deployed configuration.
Figure 21C:
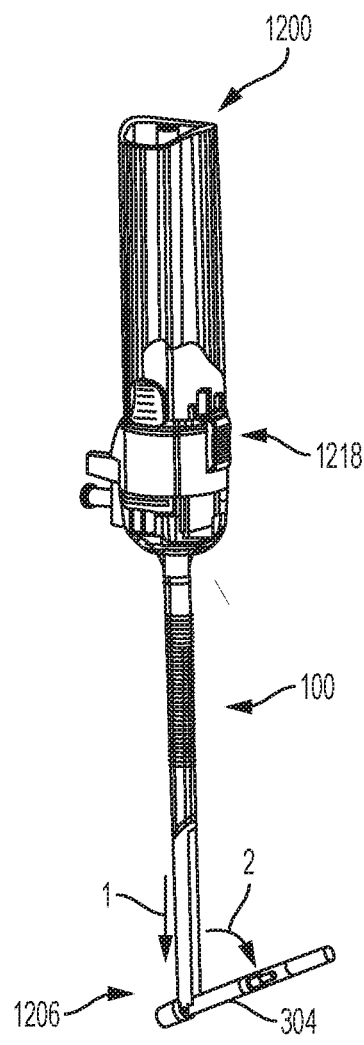
FIG. 21C is a perspective view of the device of FIG. 18B in the second, deployed configuration.

FIGS. 21A-21C illustrate the pivoting capability of the end effector retainer 1206 in greater detail. In the cross-sectional and perspective views of FIGS. 21A and 21B, respectively, the advancer 1218 is positioned at a mid-way point between its proximal-most and distal-most positions, and the end effector retainer 1206 is accordingly partially extended from a distal end of the trocar 100. As the advancer 1218 continues to be moved distally relative to the device 1200, the end effector retainer 1206 will extend fully from the distal end of the trocar 100, as shown in FIG. 21C (indicated by arrow 1). Once the end effector retainer 1206 is fully extended, however, the pivoting end cap 1226 can pivot relative to the end effector retainer housing 1224 to change the orientation of the end effector 304 attached to the pivoting end cap (indicated by arrow 2). This change in orientation of the end effector 304 can make it easier to align a percutaneously-inserted surgical instrument for coupling to the end effector. The pivoting motion can be controlled in a number of ways. For example, a control cable can be routed down the end effector retainer 1206 from a proximal end of the device and utilized to control pivoting motion. In other embodiments, the pivoting motion can be made part of the distal advancement of the end effector retainer 1206 using a cam mechanism, such that the final portion of distal travel of the advancer 1218 causes the pivoting motion. Such a configuration can have the advantage of minimizing complexity and ensuring that end effector 304 is sufficiently advanced out of the distal end of the trocar 100 before beginning the pivoting motion. Regardless of configuration utilized, any desired amount of pivoting can be provided. In embodiments utilizing a cam mechanism, a maximum amount of pivoting can be, in some cases, about 100°.

Figure 22:
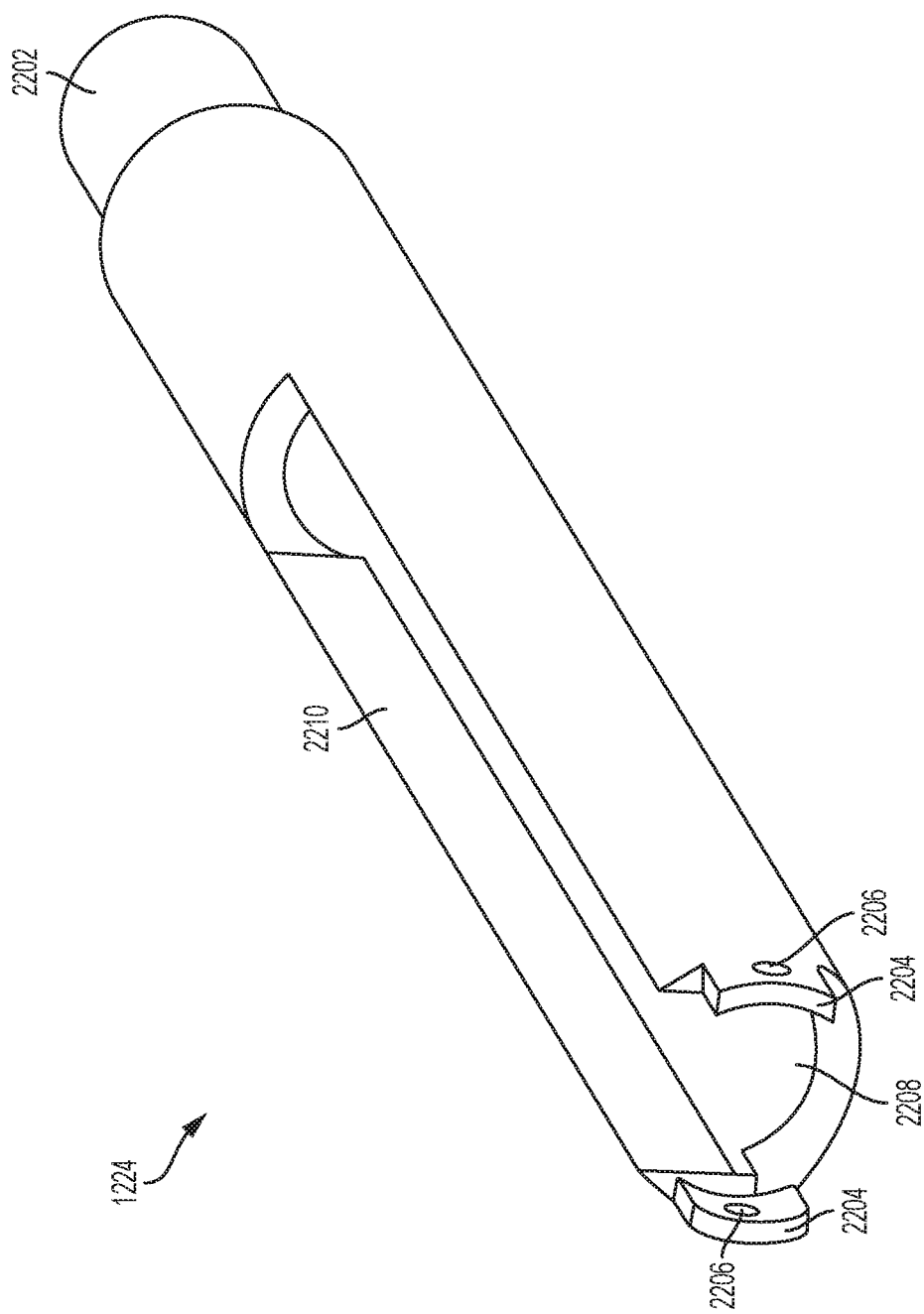
FIG. 22 is a perspective view of an end effector retainer housing of the device of FIGS. 18A and 18B.
Figure 23:
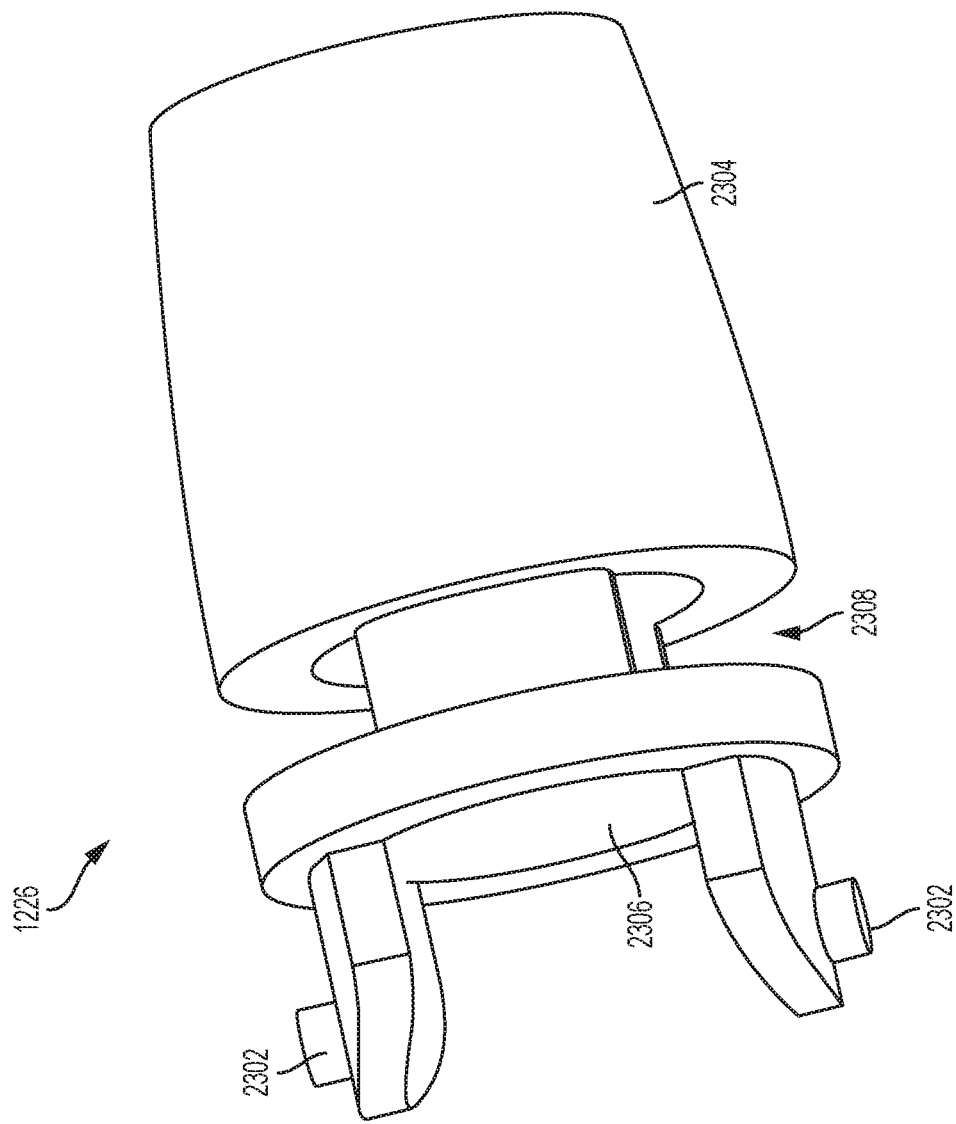
FIG. 23 is a perspective view of an end effector retainer pivoting end cap of the device of FIGS. 18A and 18B.

FIG. 22 illustrates the end effector retainer housing 1224 in greater detail. The housing 1224 can include a proximal end 2202 configured to be coupled to a distal end of the plunger component 1220 of the advancer 1218. A distal end of the housing 1224 can include opposed arms 2204 having recesses 2206 formed therein that are configured to couple with pivot pins 2302 (see FIG. 23) of the pivoting end cap 1226. The housing 1224 can have a lumen 2208 formed therein and can include a cut-out 2210 from a portion of a sidewall thereof. The lumen 2208 can be configured to receive an end effector 304 and the sidewall cut-out 2210 can be sized to allow the end effector 304 to pivot away from, or into, the housing 1224 when attached to the pivoting end cap (see FIG. 21C).

The pivoting end cap 1226 can include, as mentioned above, a proximal end having opposed pivot pins 2302 configured to be received within recesses formed in a distal end of the end effector retainer housing 1224. The pivoting end cap 1226 can have a generally cylindrical shape having an inner lumen 2306 formed therein for receiving an end effector 304. A distal portion 2304 can include a sidewall cut-out 2308 sized to receive the retention clip 1228.

Figure 24:
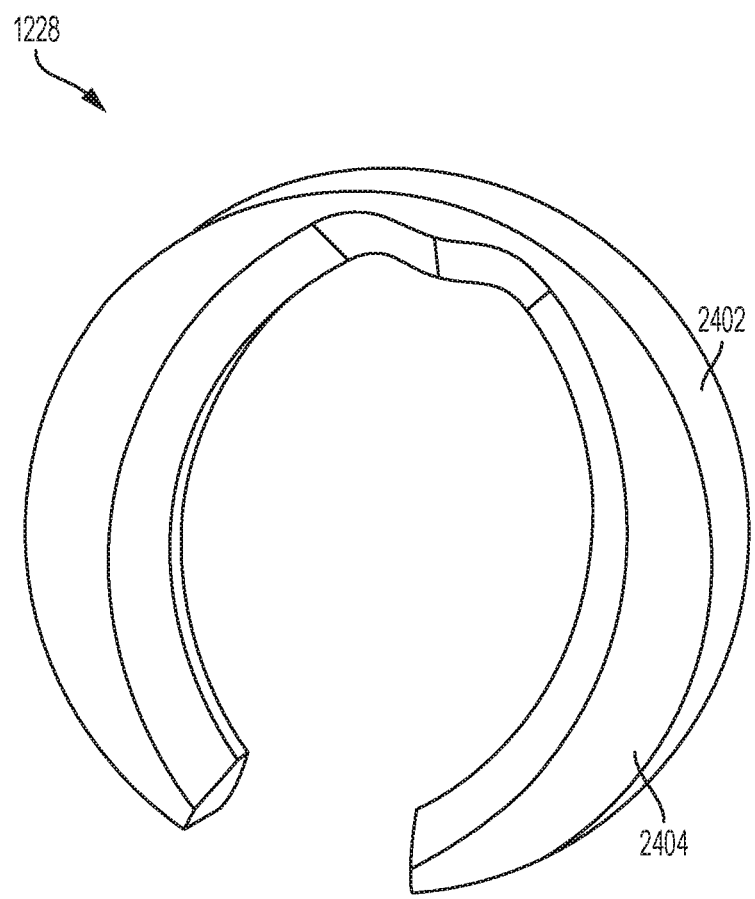
FIG. 24 is a perspective view of an end effector retainer retention clip of the device of FIGS. 18A and 18B.

The retention clip 1228, as shown in FIG. 24, can be a resilient U-shaped component, such as a snap ring or spring clip. The retention clip 1228 can be configured to be received within the sidewall cut-out 2308 formed in the pivoting end cap 1226 such that it resiliently extends into the inner lumen 2306 of the pivoting end cap. The retention clip 1228 can have a variety of shapes, sizes, and rigidities, and in some embodiments can include a two-color body arranged to provide a visual indication of end effector coupling to a surgeon or other user, as described in more detail below. In one embodiment, for example, an outer circumference 2402 of the retention clip 1228 can have a different color from an inner portion 2404 thereof.

FIGS. 25A-26B illustrate the process of coupling an end effector 304 with the end effector retainer 1206. In FIGS. 25A and 25B, the end effector 304 is aligned with, but a distance away from, the pivoting end cap 1226 of the end effector retainer 1206. As shown best in the side view of FIG. 25B, before the end effector 304 is inserted into the pivoting end cap 1226, the resilient retention clip 1228 extends into the inner lumen 2306 of the pivoting end cap. To couple the end effector 304 to the end effector retainer 1206, the end effector can be advanced into the configuration shown in FIGS. 26A and 26B. In this configuration, the insertion of the end effector 304 into the lumen 2306 of the pivoting end cap 1226 can press the retention clip 1228 radially outward relative to a longitudinal axis of the end cap. The biasing force of the retention clip 1228 can grasp the end effector 304 and prevent it from falling away from the end effector retainer 1206. Further, in some embodiments the end effector 304 can be inserted such that a recess or other feature, such as the recess 1004, aligns with the retention clip 1228. Seating the retention clip 1228 in the recess 1004 can increase the strength of the coupling between the end effector 304 and the retainer 1206.

In addition, the use of a multi-colored retention clip 1228 can provide a visual indication to a surgeon or other user when an end effector is sufficiently inserted into the end effector retainer 1206. For example, in the configuration of FIG. 25A, the retention clip 1228 is seated such that only the outer circumference surface 2402 is visible. However, in the configuration of FIG. 26A, wherein the end effector 304 is grasped by the retention clip 1228, the different-colored inner portion 2404 is visible. Seeing this different-colored surface can serve as an indication that end effector 304 is coupled to the end effector retainer 1206 and can be, for example, released from the distal end of a percutaneously-inserted surgical instrument.

Figure 27:
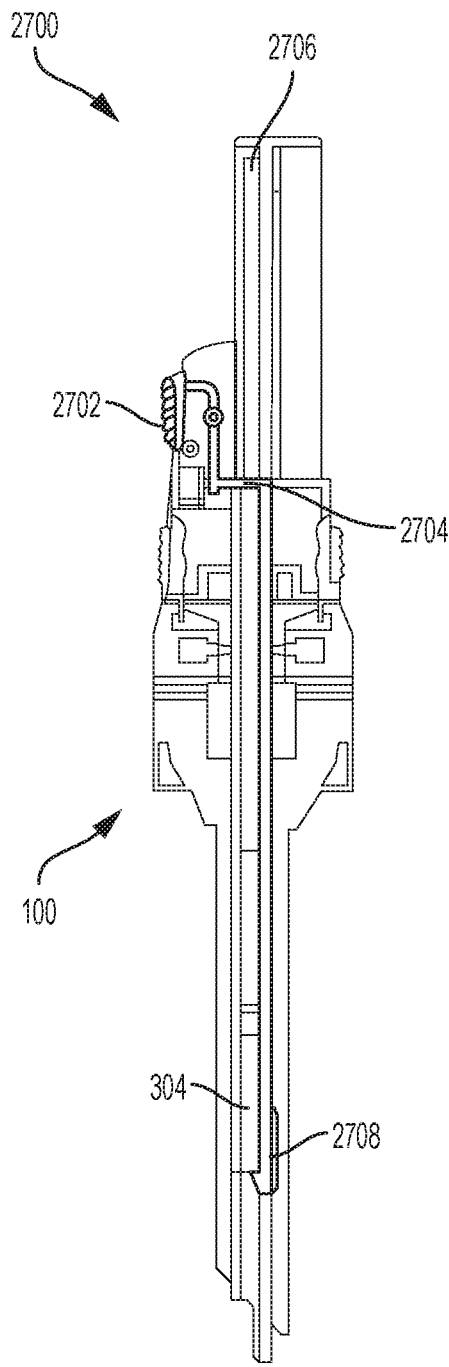
FIG. 27 is a side cross-sectional view of one embodiment of an end effector loading device that is coupled to the trocar of FIG. 1A.
Figure 28:
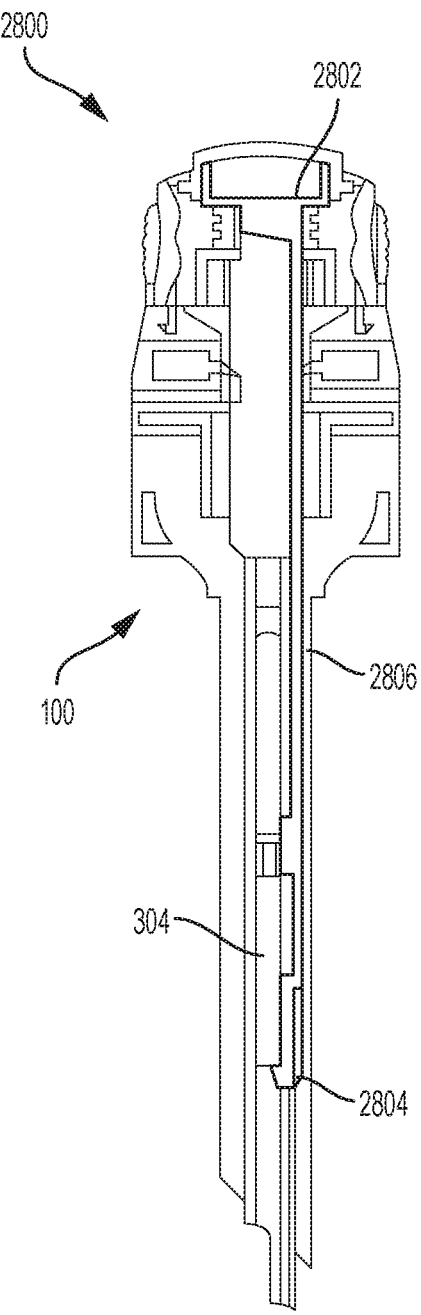
FIG. 28 is a side cross-sectional view of another embodiment of an end effector loading device that is coupled to the trocar of FIG. 1A.

Regardless of what embodiment of a loading device is utilized, it can be desirable in certain cases to provide controls near a proximal end of a loading device that permit remote deployment and release of an end effector from the device, as well as remote control of pivoting motion if provided. The actuating component 1222 of the advancer 1218 described above is one example of such a control, but a number of other possibilities also exist. FIGS. 27 and 28 illustrate additional embodiments of end effector loading devices that include controls for remotely deploying and releasing a surgical instrument end effector.

The loading device 2700 shown in FIG. 27 includes a deployment actuator 2702 (e.g., a button or other element) that can control the advancement of an end effector 304 through the trocar 100. In particular, the actuator 2702 can be linked to a sliding component 2704 such that, when actuated, the sliding component moves from a position where it blocks an inner lumen 2706 of the device 2700 to a position where it does not block the lumen 2706. Accordingly, the actuator 2702 can control the release of the end effector 304 from a proximal end of the device 2700 to a distal end of the device 2700. Further, the end effector 304 can be prevented from falling out of the loading device 2700 by a latch 2708 disposed at a distal end of the device. The latch 2708 can be configured such that a percutaneously-inserted surgical instrument moves the latch radially outward away from the end effector 304 when a distal end of the instrument is inserted into a distal end of the loading device 2700 and into a socket formed in the end effector 304. In such a configuration, the latch 2708 is only released when the surgical instrument has coupled with the end effector 304.

FIG. 28 illustrates another embodiment of an end effector loading device 2800 that includes a proximally-positioned control for remotely releasing an end effector 304 from a distal end of the loading device. In particular, the loading device 2800 includes an actuator 2802, such as a button, that is coupled to a latch 2804 by a linkage 2806. The latch 2804 extends into a lumen 2808 of the device 2800 and prevents the end effector 304 from exiting the lumen. Pressing or otherwise actuating the button or other actuator 2802 can urge the latch 2804 to move radially outward and free the end effector 304.

While the various embodiments described above may have only subset of the features described herein, the various components and functionalities described can be combined in a variety of manners, all of which are considered within the scope of the present invention. For example, a loading device could include both the translating advancer and pivoting end effector retainer of the device 1200, as well as a control to remotely release the end effector from the retainer, similar to the control shown in the device 2800.

The devices described herein can be utilized in a variety of surgical procedures. In general, a method of using the devices described herein can include coupling a loading device with a surgical trocar such that a lumen formed in the loading device coaxially aligns with a working channel of the surgical trocar and complementary mating features on the loading device and the surgical trocar restrict relative motion therebetween. Coupling the loading device to the trocar can occur after coupling a surgical end effector to the loading device, or the loading device can come pre-assembled with a surgical end effector, or the loading device can be inserted without an end effector in anticipation of receiving one from a percutaneously-inserted surgical instrument (e.g., at the conclusion of a procedure or when one end effector is to be exchanged for another). As mentioned above, the coupling of the loading device and the trocar can make use of pre-existing mating features formed on or in the trocar for attachment of other accessories, such as an obturator.

Methods of using the devices described herein can further include passing an end effector received within a lumen of the loading device through the working channel of the surgical trocar. This can be accomplished by virtue of the coupling described above (e.g., if the end effector is coupled to a distal end of the loading device as with the device 300), or can include actuating an advancer to deploy the end effector distally beyond a distal end of the trocar. Furthermore, the method can include selectively releasing the end effector from the lumen of the loading device, e.g., after the end effector has been coupled to a distal end of a surgical instrument in vivo.

In certain embodiments, it may not be desirable to utilize a loading device as described above, or one may not be available for use. In such a case, a distal tip of a surgical instrument is often "reverse" passed through a trocar from inside the patient's body to outside the patient's body, thereby permitting a surgeon or other user to directly manipulate the distal end of the surgical instrument and the end effector when coupling, de-coupling, or exchanging the end effector. Passing the distal end of a surgical instrument (with or without an end effector attached) from a distal end of a trocar to a proximal end of the trocar can easily damage the various seals disposed across the working channel of the trocar, as described above.

Figure 29:
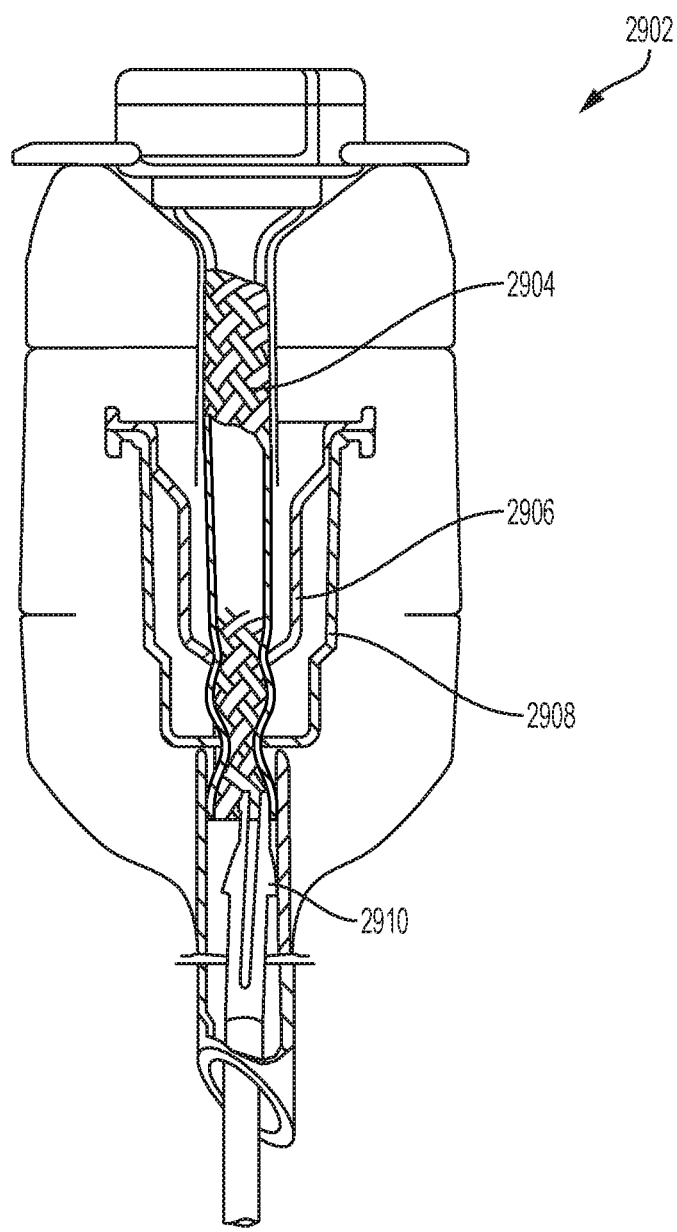
FIG. 29 is a side cross-sectional view of one embodiment of a trocar seal protector.

To protect the trocar seals, a seal protector can be employed, as shown in FIG. 29. More particularly, a trocar 2902 can be fitted with a seal protector 2904 that extends from a proximal side of any trocar seals 2906, 2908 to a distal side thereof. The seal protector 2904 can be a tubular element having a conical distal end oriented to expand toward a distal end of the trocar. The seal protector 2904 material can be deformable and elastic, such that the seal protector can be deformed as it is passed through the seals 2906, 2908, but can return to its conical shape (at least at the distal end thereof) to protect the distal-facing side of the seals 2906, 2908. Further, the seal protector 2904 material can be compressible such that the seals 2906, 2908 can continue to operate as intended. In one embodiment, for example, the seal protector can be a thin polypropylene woven cannula wrapped in a thin polypropylene film. This construction can be advantageous because, at the position of the seals 2906, 2908, the woven cannula can neck down and the polypropylene film can rupture, allowing the seal to continue to close as intended. On a distal side of the seals 2906, 2908, however, the woven cannula can spring back into place.

With the seal protector 2904 in place and a flared distal end facing toward a distal end of the trocar 2902, any percutaneously-inserted surgical instrument, such as instrument 2910, can be received within the seal protector 2904 when it is passed proximally through a distal end of the trocar 2902. The seal protector 2904 can then protect against any portion of the surgical instrument 2910 catching or snagging on the seals 2906, 2908 and causing damage thereto. As a result, surgeons or other users can continue to pass instrument 2910 through the trocar 2902 to exchange end effectors outside the patient's body without damaging the trocar 2902.

Any of the components and devices known in the art and/or described herein can be provided as part of a kit including any of a loading device, a trocar, and a surgical end effector, as described herein, as well as other components with which such components are typically used, e.g., an obturator. The loading device can be configured to be removably coupled to the trocar using one or more complementary mating features or elements present on the trocar and the loading device. The trocar can be any particular model or configuration of trocar known in the art. Further, the end effectors provided in the kit can perform different functions, including but not limited to the functions described herein, and/or can be included together in a single kit to perform a particular function, such as a kit specifically tailored for stretching and stapling tissue. Further, one or more other ports or surgical instruments, including cameras and other viewing instruments, can be provided to assist in performing a given procedure.

The devices disclosed herein can be formed from a variety of materials and can have a variety of different sizes and shapes. For example, loading devices and trocars can be formed from various polymers and/or metals. Furthermore, particular components can be formed from a different material than other components. By way of further example, a loading device housing can be formed from a polymer material, (e.g., polycarbonate), while an end effector retainer (e.g., the pivoting end effector retainer 1206) can be formed from a metal, such as surgical grade stainless steel (e.g., 17-4), other 300 and 400 series stainless steels, titanium, and aluminum, perhaps to take advantage of greater rigidity. Of course, these are just non-limiting examples of possible material combinations. Device sizes can also vary greatly, depending on the intended use and surgical site anatomy. As mentioned above, the devices described herein can commonly be used in connection with trocar diameters on the order of 5 mm, though any particular size could be constructed. Further, a variety of lengths could be employed at any particular diameter to accommodate various end effector sizes, surgical site locations, etc.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical instrument kit, comprising:
   a trocar comprising a trocar housing, a trocar shaft extending distally from the trocar housing, and a working channel extending at least partially through the trocar housing and the trocar shaft, the trocar housing having at least one mating element;
   an obturator device comprising an obturator handle and an obturator shaft extending distally from the obturator handle, the obturator handle having at least one mating element that is configured to selectively couple to the at least one mating element of the trocar housing when the obturator shaft is disposed within the working channel of the trocar shaft;
   a loading device having a loading device housing and a loading device shaft extending distally from the loading device housing, the loading device housing having at least one mating element that is configured to selectively couple to the at least one mating element of the trocar housing when the loading device shaft is disposed within the working channel of the trocar shaft, the loading device housing and shaft having a lumen extending therethrough;
   an end effector retainer disposed on a distal end of the loading device shaft; and
   an end effector configured to be passed through the lumen in the loading device housing and shaft and selectively coupled to the end effector retainer;
   wherein the end effector retainer is configured to pivot relative to the loading device to cause a coupled end effector to pivot such that the coupled end effector can mate to a separate surgical instrument and decouple from the loading device.

2. The kit of claim 1, further comprising an advancer slidably disposed within the lumen of the loading device and configured to translate the end effector along a longitudinal axis of the lumen.

3. The kit of claim 2, further comprising an actuator coupled to the advancer and configured to indicate when the advancer reaches a distal-most position relative to the lumen.

4. The kit of claim 1, further comprising an actuator positioned in the loading device housing and coupled to the end effector retainer to selectively release the surgical end effector.

5. The kit of claim 4, wherein the end effector retainer includes a latch and the actuator is coupled to the latch by a linkage.

6. The kit of claim 1, wherein the end effector retainer includes at least one projection configured to be received within at least one recess formed in the end effector.

7. The kit of claim 1, wherein the loading device includes at least one viewport to permit visualization of a position of the end effector within the lumen.

* * * * *